(12) United States Patent
Cai et al.

(10) Patent No.: US 7,842,805 B2
(45) Date of Patent: Nov. 30, 2010

(54) PHARMACEUTICAL COMPOUNDS AS ACTIVATORS OF CASPASES AND INDUCERS OF APOPTOSIS AND THE USE THEREOF

(75) Inventors: Sui Xiong Cai, San Diego, CA (US); Mark B. Anderson, Salt Lake City, UT (US); Adam Willardsen, Sandy, UT (US); Songchun Jiang, San Diego, CA (US); Robert J. Halter, Salt Lake City, UT (US); Rachel Slade, Salt Lake City, UT (US); Yevgeniya Klimova, Sandy, UT (US)

(73) Assignees: Myrexis, Inc., Salt Lake City, UT (US); EpiCept Corporation, Tarrytown, NY (US)

( * ) Notice: Subject to any disclaimer, the term of this patent is extended or adjusted under 35 U.S.C. 154(b) by 0 days.

(21) Appl. No.: 11/773,293

(22) Filed: Jul. 3, 2007

(65) Prior Publication Data

US 2008/0020985 A1 Jan. 24, 2008

Related U.S. Application Data

(63) Continuation of application No. PCT/US2006/000176, filed on Jan. 3, 2006.

(60) Provisional application No. 60/641,356, filed on Jan. 3, 2005.

(51) Int. Cl.
*C07D 403/12* (2006.01)
*C07D 253/08* (2006.01)
*A61K 31/53* (2006.01)
*A61P 35/00* (2006.01)

(52) U.S. Cl. ..................... 544/180; 514/241
(58) Field of Classification Search ............... 544/180; 514/241
See application file for complete search history.

(56) References Cited

U.S. PATENT DOCUMENTS

| 6,235,752 | B1 | 5/2001 | Yuan et al. |
| 6,492,360 | B1 | 12/2002 | Napoletano et al. |
| 6,498,159 | B1 | 12/2002 | Watanabe et al. |
| 6,514,971 | B1 | 2/2003 | Thomas et al. |
| 6,589,951 | B1 | 7/2003 | Napoletano et al. |
| 2004/0176603 | A1 | 9/2004 | Priepke et al. |

FOREIGN PATENT DOCUMENTS

| EP | 0049029 | 4/1982 |
| JP | 02129183 | 5/1990 |

OTHER PUBLICATIONS

Cecil Textbook of Medicine, edited by Bennet, J.C., and Plum F., 20th edition, vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Wood et al., Current Opinion in Pharmacology, 1,370-377, 2001.*
Andoh et al., Advances in Pharmacology, 29B, 93-103, 1994.*
Denny et al., Expert Opin. Emerg. Drugs, 9(1), 105-133, 2004.*
Ruchelman et al., Biorganic & Medicinal Chemistry, 12, 795-806, 2004.*
Jordan et al., Biochemistry 39(29), 8593-8602, 2000.*
Chen et al., Biochemistry 37(51), 17735-17744, 1998.*
Gilbert et al., Journal of Heterocyclic Chemistry, 6(6), 779-782, 1969.*
Clark et al., Journal of Chemical Research Synopsis, 2, 62-63, 1984; CA 101: 6506, 1984.*
Bold et al., "New anilinophthalzines as potent and orally well absorbed inhibitors of the VEGF receptor tyrosine kinases useful as antagonists of tumor-driven angiogenesis", *Journal of Medicinal Chemistry*, 2000, 43(16):3200.
Bold et al., "New anilinophthalzines as potent and orally well absorbed inhibitors of the VEGF receptor tyrosine kinases useful as antagonists of tumor-driven angiogenesis", *Journal of Medicinal Chemistry*, 2000, 43(12):2310-2323.
Bystrkh et al., "Spectra and structure of 1-aminophthalazines", *Khimiya Geterotsiklicheskikh Soedinenii*, 1983, 6:826-833.
Dalla Croce, "Reactivity of Me Cholor(phenylhydrazono)acetate with some diazines", *Journal of Heterocyclic Chemistry*, 1975, 12(6):1133-1134.

* cited by examiner

*Primary Examiner*—Venkataraman Balasubramanian
(74) *Attorney, Agent, or Firm*—Kelly A. Echols; Herbert L. Ley, III; I.P. Group; Myrexis, Inc.

(57) ABSTRACT

Disclosed are 1-arylamino-phthalazines, 4-arylamino-benzo[d][1,2,3]triazines, and analogs thereof effective as activators of caspases and inducers of apoptosis. The compounds of this invention are useful in the treatment of a variety of clinical conditions in which uncontrolled growth and spread of abnormal cells occurs.

14 Claims, No Drawings

PHARMACEUTICAL COMPOUNDS AS ACTIVATORS OF CASPASES AND INDUCERS OF APOPTOSIS AND THE USE THEREOF

CROSS REFERENCE TO RELATED U.S. APPLICATION

This application is a continuation of international patent application no. PCT/US06/000176, filed Jan. 3, 2006, which claims the benefit of U.S. Provisional Application Ser. No. 60/641,356, filed on Jan. 3, 2005, each of which are incorporated herein by reference in their entirety.

FIELD OF THE INVENTION

This invention is in the field of medicinal chemistry. In particular, the invention relates to compounds that are activators of caspases and inducers of apoptosis. The invention also relates to the use of these compounds as therapeutically effective anti-cancer agents.

BACKGROUND OF THE INVENTION

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. M phase specific antineoplastic drugs, such as vinblastine and paclitaxel, are known to affect tubulin polymerization. The ability of cells to appropriately polymerize and depolymerize tubulin is thought to be an important activity for M phase cell division.

Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that 1-arylamino-phthalazines, 4-arylamino-benzo[d][1,2,3]triazine, and analogs, as represented in Formulae I-VIII below, are activators of the caspase cascade leading to the activation of caspase-3 and inducers or promoters of apoptosis. Thus, they are useful in treating or delaying the onset of diseases and disorders that are responsive to the activation of the caspase cascade or to the induction of apoptosis.

Accordingly, one aspect of the present invention is directed to the use of compounds of the present invention in inducing capase activities, particularly caspase-3 activities, and inducing or promoting apoptosis, and in inhibiting tubulin, by administering the compounds to cells in vitro or in vivo in warm-blood animals, particularly mammals.

Another aspect of the present invention is to provide a method for treating or delaying the onset of diseases and disorders that are responsive to inhibition of tubulin including but not limited to neoplastic diseases (such as cancer), psoriasis, autoimmune diseases, and fungi infection. The method comprises administering to a subject mammal in need of the treatment a therapeutically effective amount of a compound of the present invention.

Many of the compounds as represented by Formulae I-VIII below are novel compounds. Therefore, another aspect of the present invention is to provide novel compounds, and to also provide for the use of these novel compounds for treating, preventing or ameliorating neoplasia and cancer.

Yet another aspect of the present invention is to provide a pharmaceutical composition useful for treating disorders responsive to the inhibition of tubulin and the induction of apoptosis, containing an effective amount of a compound of the present invention, preferably in admixture with one or more pharmaceutically acceptable carriers or diluents.

In yet another aspect of the present invention, methods are provided for the preparation of the novel compounds of the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

It has been discovered that compounds of the present invention are potent and highly efficacious activators of the caspase cascade particularly caspase-3, and inducers of apoptosis. Therefore, the compounds are useful for treating diseases and disorders responsive to induction of apoptosis and/or inhibition of tubulin.

Thus, the present invention provides a method of inhibiting tubulin in cells in vitro or in warm-blood animals, particularly mammals, more particularly humans. As used herein, the term "inhibiting tubulin" means inhibiting the polymerization (or assembly) of tubulin monomers or promoting depolymerization of microtubules (i.e., tubulin disassembly). Inhibition of tubulin can be assayed, e.g., by the method described in Example 31 below. In addition, the present invention also provides a method of activating caspase, particularly caspase-3 and inducing apoptosis in cells in vitro or in warm-blood animals, particularly mammals, more particularly humans. The term "activating caspase" as used herein means activating or enhancing the enzymatic (protease) activity of a caspase (e.g., caspase-3), which, if occurring inside cells, results in promoted apoptosis or cell death. The ability of a compound in activating caspase, particularly caspase-3, can be assayed in a method as provided in Example 29 below. The term "inducing apoptosis" as used herein means inducing apoptosis in cells so as to cause cell death. The ability of a compound to induce apoptosis can be tested in a method as described in Example 33 below. Also provided are methods for treating or delaying the onset of diseases and disorders responsive to inhibiting tubulin, activating caspase-3, or inducing apoptosis. Specific examples of such diseases and disorders are provided in details below.

The above various methods of the present invention can be practiced by or comprise treating cells in vitro or a warm-blood animal, particularly mammal, more particularly a human with an effective amount of a compound according to the present invention. As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human, a pharmaceutical composition comprising an effective amount of a compound according to the present invention.

Specifically, the methods of the present invention comprise treating cells in vitro or a warm-blood animal, particularly mammal, more particularly a human with an effective amount of a compound according to Formula I:

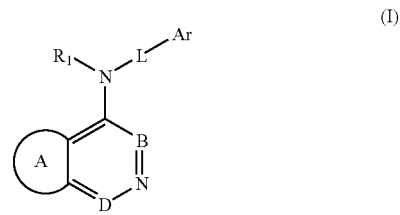

or a pharmaceutically acceptable salt or solvate thereof, wherein:

Ar is aryl or heteroaryl; each of which is optionally substituted by one or more same or different substituents defined for $R_{12}$;

L is —$(CR_aR_b)n$- or —$N(R_a)C(=O)$— wherein n is 0, 1 or 2, and $R_a$ and $R_b$ independently are H or optionally substituted alkyl, for example, methyl, ethyl, propyl, isopropyl, $C_{1-4}$ haloalkyl (e.g., trifluoromethyl);

$R_1$ is $C_{1-6}$ alkyl, preferably methyl or ethyl, more preferably methyl;

A is an aromatic (e.g., phenyl), heteroaromatic (e.g., a five or six-membered heteroaryl ring having 1, 2 or 3 heteroatoms independently selected from O, N and S), heterocyclic (e.g., 3 to 7-membered heterocycle ring having 1, 2 or 3 heteroatoms independently selected from O, N and S), or carbocyclic (e.g., 3 to 7-membered) ring; each of which is optionally substituted by one or more same or different substituents defined for $R_{12}$;

B is nitrogen or $CR_{12}$;

D is nitrogen or $CR_{13}$; and $R_{12}$ and $R_{13}$ are independently selected from:
  (a) H, halo, $N_3$, nitro, hydroxy, thiol, and CN,
  (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, $OC(=O)N(R^{50})(R^5)$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$,
  (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{52})(R^{53})$, —$N(R^{52})C(=O)R_{42}$, —$N(R^{52})C(=O)N(R^{52})(R^{53})$, —$C(=O)N(R^{52})(R^{53})$, $OC(=O)N(R^{52})(R^{53})$, $R_{42}C(=O)$—, $R_{42}C(=O)O$—, $R_{42}C(=G^1)$-, $R_{42}C(=G^1)G^2$-, $R_{42}C(=G^1)G^2(R^{52})$—, —$C(=G^1)G^2R_{43}$, or -$G^4C(=G^1)G^2R_{43}$,
  (d) —$N(R^{50})(R^{51})$, —$N(R^{50})C(=O)R_{40}$, —$N(R^{50})C(=O)N(R^{50})(R^{51})$, —$C(=O)N(R^{50})(R^{51})$, $OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$, $G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, $OH(R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl; and $R^{52}$ and $R^{53}$ are independently H, $OH(R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl.

In one embodiment of methods utilizing compounds of Formula I, the compounds are not (4-chloro-phenyl)-N-methyl-(4-pyridin-4-ylmethyl-phthalazin-1-yl)-amine. In another embodiment of methods utilizing compounds of Formula I, when D is $CR_{13}$ then $R_{13}$ is not aryl, heteroaryl, arylalkyl, or heteroarylalkyl.

Another group of compounds useful in the various methods of the present invention are those represented by Formula II:

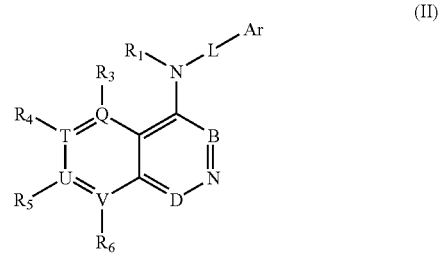

or pharmaceutically acceptable salts or solvates thereof, wherein:

Ar is aryl or heteroaryl; each of which is optionally substituted by one or more substituents;

L is —$(CR_aR_b)n$- or —$N(R_a)C(=O)$— wherein n is 0, 1 or 2, and $R_a$ and $R_b$ independently are H or optionally substituted alkyl, for example, methyl, ethyl, propyl, isopropyl, $C_{1-4}$ haloalkyl (e.g., trifluoromethyl);

$R_1$ is $C_{1-6}$ alkyl, preferably methyl or ethyl, more preferably methyl;

B is nitrogen or $CR_{12}$;

D is nitrogen or $CR_{13}$;

$R_3$-$R_6$, $R_{12}$, and $R_{13}$ are independently selected from:
  (a) H, halo, $N_3$, nitro, hydroxy, thiol, and CN,
  (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, $OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$, (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C(=$G^1$)$G^2R_{43}$, or -$G^4$C(=$G^1$)$G^2R_{43}$, (d) —N($R^{50}$)($R^{51}$), —N($R^{50}$)C(=O)$R_{40}$, —N($R^{50}$)C(=O)N($R^{50}$)($R^{51}$), C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=G)$G^2$($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

R42 is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle (e.g., piperidinyl, pyrrolidinyl, and morpholinyl), wherein $R^{50}$ and $R^{51}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and Q, T, U, and V are independently nitrogen or carbon provided that when Q, T, U, or V is nitrogen then there is no substituent at the nitrogen.

In specific embodiments, $R_1$ is $C_{1-2}$ alkyl, (e.g. $CH_3$). In specific embodiments, $R_3$-$R_6$, $R_{12}$, and $R_{13}$ are independently $R_{14}$, $OR_{14}$, $SR_{14}$ or $NR_{14}R_{15}$, wherein $R_{14}$ and $R_{15}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy (e.g., methylenedioxy). In specific embodiments, $R_5$ is H, F, or $C_{1-3}$ alkyl, preferably H or F, and more preferably H.

In one embodiment of methods utilizing compounds of Formula II, the compounds are not (4-chloro-phenyl)-N-methyl-(4-pyridin-4-ylmethyl-phthalazin-1-yl)-amine. In another embodiment of methods utilizing compounds of Formula II, when D is $CR_{13}$ then $R_{13}$ is not aryl, heteroaryl, araylalkyl, or heteroarylalkyl.

Another group of compounds useful in the various methods of the present invention are those represented by Formula III:

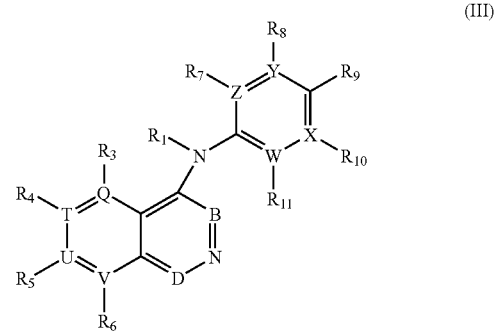

(III)

or pharmaceutically acceptable salts or solvates thereof, wherein:

$R_1$ is $C_{1-6}$ alkyl, preferably methyl or ethyl, more preferably methyl;

B is nitrogen or $CR_{12}$;

D is nitrogen or $CR_{13}$;

$R_3$-$R_{13}$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)

C(=O)R$_{42}$, —N(R$^{52}$)C(=O)N(R$^{52}$)(R$^{53}$), —C(=O)N(R$^{52}$)(R$^{53}$), OC(=O)N(R$^{52}$)(R$^{53}$), R$_{42}$C(=O)—, R$_{42}$C(=O)O—, R$_{42}$C(=G$^1$)-, R$_{42}$C(=G$^1$)G$^2$-, R$_{42}$C(=G$^1$)G$^2$(R$^{52}$)—, —C(=G$^1$)G$^2$R$_{43}$, or -G$^4$C(=G$^1$)G$^2$R$_{43}$, (d) —N(R$^{50}$)(R$^{51}$), —N(R$^{50}$)C(=O)R$_{40}$, —N(R$^{50}$)C(=O)N(R$^{50}$)(R$^{51}$), C(=O)N(R$^{50}$)(R$^{51}$), —OC(=O)N(R$^{50}$)(R$^{51}$), R$_{40}$C(=O)—, R$_{40}$C(=O)O—, R$_{40}$C(=G$^1$)-, R$_{40}$C(=G$^1$)G$^2$-, R$_{40}$C(=G$^1$)G$^2$(R$^{50}$)—, —C(=G$^1$)G$^2$R$_{41}$ or -G$^3$C(=G$^1$)G$^2$R$_{41}$,

G$^1$ is S or N; G$^2$ and G$^3$ are independently S or N(R$^{50}$); G$^4$ is N(R$^{52}$);

R$_{40}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_3$, nitro, hydroxy, thiol, CN, C$_{1-6}$ alkyl, carbocycle, heterocycle, aryl and heteroaryl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_3$, nitro, hydroxy, thiol, CN, C$_{1-6}$ alkyl, carbocycle, heterocycle, aryl and heteroaryl;

R$_{42}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_3$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_3$, nitro, hydroxy, thiol, CN and C$_{1-6}$ alkyl;

R$^{50}$ and R$^{51}$ are independently H, OH (R$^{50}$ and R$^{51}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, carbocycle, heterocycle, aryl, heteroaryl, or R$^{50}$ and R$^{51}$ together with the nitrogen atom to which they are both linked form a 3, 4, 5 or 6-membered heterocycle (e.g., piperidinyl, pyrrolidinyl, and morpholinyl), wherein R$^{50}$ and R$^{51}$ each is optionally substituted with one to three substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$ and R$^{53}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$^{52}$ and R$^{53}$ together with the nitrogen atom to which they are both linked form a 3, 4, 5 or 6-membered heterocycle (e.g., piperidinyl, pyrrolidinyl, and morpholinyl), wherein R$^{52}$ and R$^{53}$ each is optionally substituted with one to three substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and Q, T, U, V, W, X, Y, and Z are independently nitrogen or carbon provided that when Q, T, U, V, W, X, Y, or Z are nitrogen then there is no substituent at the nitrogen.

In specific embodiments, R$_1$ is C$_{1-2}$ alkyl, (e.g. CH$_3$). In specific embodiments, R$_3$, R$_4$, R$_6$-R$_8$, R$_{10}$-R$_{13}$ are independently R$_{14}$, OR$_{14}$, SR$_{14}$ or NR$_{14}$R$_{15}$, wherein R$_{14}$ and R$_{15}$ are independently H, halo, hydroxyl, carboxyl, C$_{1-6}$ alkyl, C$_{2-6}$ alkenyl, C$_{2-6}$ alkynyl, or C$_{1-6}$ haloalkyl; wherein any of the groups are optionally substituted with one or more halo, C$_{1-6}$ haloalkyl, C$_1$-C$_6$ alkyl, C$_2$-C$_6$ alkenyl, C$_2$-C$_6$ alkynyl, C$_1$-C$_6$ hydroxyalkyl, nitro, amino, ureido, cyano, C$_{1-6}$ acylamino, hydroxy, thiol, C$_{1-6}$ acyloxy, azido, C$_1$-C$_6$ alkoxy, carboxy or C$_{1-2}$ alkylenedioxy (e.g., methylenedioxy). In specific embodiments, R$_5$ is H, F, or C$_{1-3}$ alkyl, preferably H or F, and more preferably H.

In additional specific embodiments, R$_9$ is H; OH; halo; N$_3$; C$_{1-6}$ alkyl; C$_{1-6}$ haloalkyl-OR$_{9a}$, wherein R$_{93}$ is C$_{1-6}$ alkyl or C$_{1-6}$ haloalkyl; —NH(R$^a$) or —N(R$^a$)(R$^b$) where R$^a$ and R$^b$ are independently C$_{1-6}$ alkyl, C$_{1-6}$ acyl, C$_{1-6}$ acyloxy, amino, —(C=O)N(R$^c$)(R$^d$) wherein R$^c$ and R$^d$ are independently H or C$_{1-6}$ alkyl; or —COOR$_{9b}$, wherein R$_{9b}$ is C$_{1-6}$ alkyl; optionally R$_9$ and one of R$_8$ and R$_{10}$ together form a 3, 4, 5, or 6-membered heterocycle; and any of the groups are optionally substituted with one or more halo, C$_{1-6}$ haloalkyl, C$_1$-C$_6$ alkyl, C$_2$-C$_6$ alkenyl, C$_2$-C$_6$ alkynyl, C$_1$-C$_6$ hydroxyalkyl, nitro, amino, ureido, cyano, C$_{1-6}$ acylamino, hydroxy, thiol, C$_{1-6}$ acyloxy, azido, C$_1$-C$_6$ alkoxy, carboxy or C$_{1-2}$ alkylenedioxy (e.g., methylenedioxy).

In one embodiment of methods utilizing compounds of Formula III, the compounds are not (4-chloro-phenyl)-N-methyl-(4-pyridin-4-ylmethyl-phthalazin-1-yl)-amine. In another embodiment of methods utilizing compounds of Formula III, when D is CR$_{13}$ then R$_{13}$ is not aryl, heteroaryl, arylalkyl, or heteroarylalkyl.

One specific group of compounds useful in the various methods of the present invention are those represented by Formula IIIa-IIId:

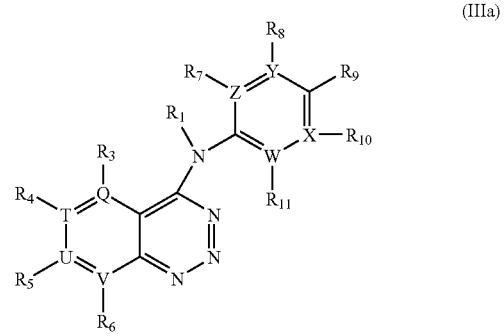

(IIIa)

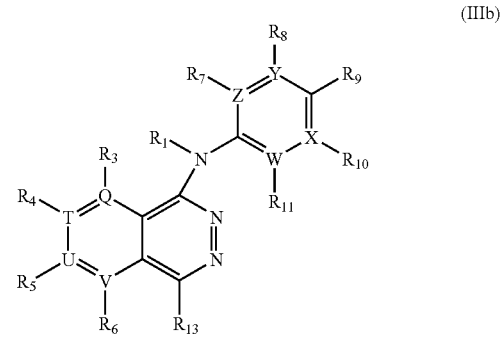

(IIIb)

-continued (IIIc)
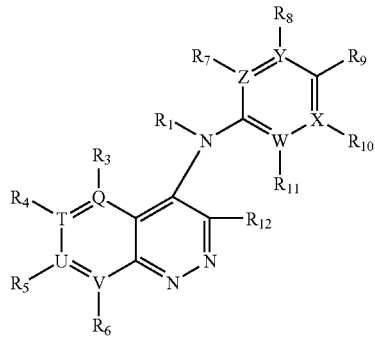

(IIId)
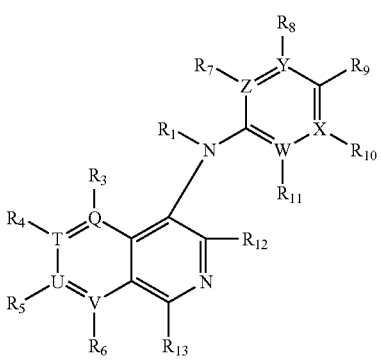

or pharmaceutically acceptable salts or solvates thereof, wherein $R_1$, $R_3$-$R_{13}$, Q, T, U, V, W, X, Y and Z are defined as above in Formula III.

Another specific group of compounds useful in the various methods of the present invention are those represented by Formula IV-VIII:

(IV)
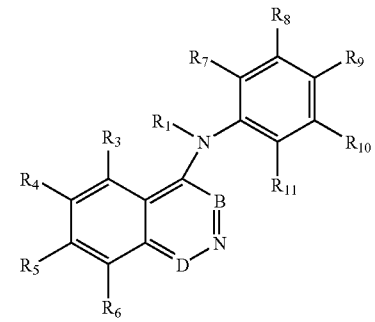

(V)
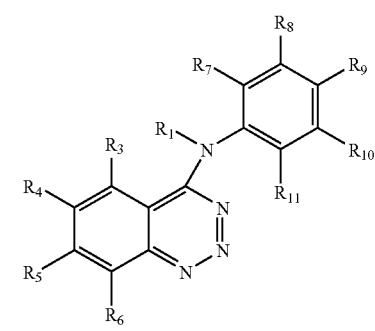

(VI)
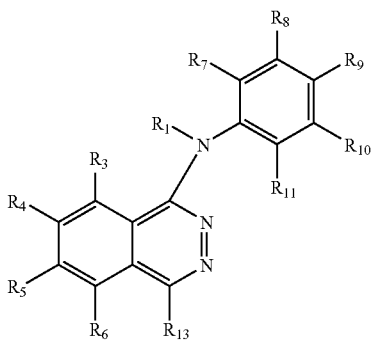

(VII)
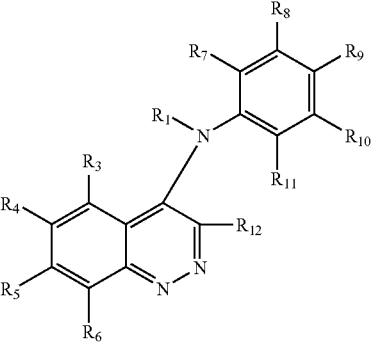

(VIII)
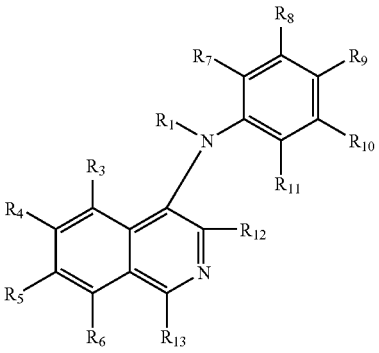

or pharmaceutically acceptable salts or solvates thereof, wherein $R_1$, $R_3$-$R_{11}$, B and D are defined as above in Formula III.

In specific embodiments of Formulae I-ITT and IV, B is nitrogen and D is $CR_{13}$ where $R_{13}$ is as defined for Formula III above. In specific embodiments of Formulae I-ITT and IV, D is nitrogen and B is $CR_{12}$ where $R_{12}$ is as defined for Formula III above. In other specific embodiments of Formulae I-ITT and IV, B and D are nitrogen. In specific embodiments of Formulae II and III-IIId, one of Q, T, U, and V are nitrogen. In other embodiments of Formulae II and III-IIId, two of Q, T, U, and V are nitrogen (e.g., Q and T are nitrogen, U and V are nitrogen, Q and V are nitrogen, T and U are nitrogen, T and V are nitrogen, or Q and V are nitrogen). In specific embodiments of Formula II-IIId, one of W, X, Y, and Z is nitrogen. In specific embodiments of Formula II-IIId, two of W, X, Y, and Z are nitrogen (e.g., W and X are nitrogen, W and Y are nitrogen, W and Z are nitrogen, or X and Y are nitrogen).

The present invention also provides novel compounds, which are potent caspase-3 activators and/or apoptosis inducers/promoters, and/or tubulin inhibitors. Specifically, novel compounds of the present invention include compounds of Formulae I-VIII provided that the compound is not:
(4-chloro-phenyl)-N-methyl-(4-pyridin-4-ylmethyl-phthalazin-1-yl)-amine;
4-(3-chloro-4-methoxy-benzylamino)-1-(methyl-pyridin-2-yl-amino)-phthalazine-6-carbonitrile;
(4-imidazol-1-yl-phthalazin-1-yl)-N-methyl-phenylamine;
(4-chloro-phenyl)-(4-imidazol-1-yl-phthalazin-1-yl)-N-methyl-phenylamine;
(3-chloro-phenyl)-(4-imidazol-1-yl-phthalazin-1-yl)-N-methyl-phenylamine;
(4-imidazol-1-yl-phthalazin-1-yl)-N-ethyl-phenylamine;
(4-fluoro-phenyl)-(4-imidazol-1-yl-phthalazin-1-yl)-N-ethyl-phenylamine;
(4-chloro-phenyl)-(4-imidazol-1-yl-phthalazin-1-yl)-N-ethyl-phenylamine;
(4-chloro-phthalazin-1-yl)-N-methyl-phenylamine;
(4-chloro-phthalazin-1-yl)-N-ethyl-phenylamine; or
2-{4-[(3-bromo-cinnolin-4-yl)-N-methylamino]-phenoxy}-propionic acid ethyl ester.

In another embodiment, novel compounds of the present invention include compounds of Formulae I-VIII provided that: (1) when $R_{13}$ is present then $R_{13}$ is not aryl, heteroaryl, arylalkyl, heteroarylalkyl, or amino substituted by aryl, heteroaryl, arylalkyl, or heteroarylalkyl; (2) when $R_{12}$ is present then $R_9$ is not —O($C_{1-6}$ alkyl)C(O)O($C_{1-6}$ alkyl); and (3) the compound is not (4-chloro-phthalazin-1-yl)-N-methyl-phenylamine or (4-chloro-phthalazin-1-yl)-N-ethyl-phenylamine.

In specific embodiments, $R_9$ is not —O($C_{1-6}$ alkyl)C(O)O ($C_{1-6}$ alkyl) or halo, and when $R_9$ is H then $R_8$ and $R_{10}$ are not H or halo. Preferably, $R_9$ is selected from the group:

—$OR_{19}$, wherein $R_{19}$ is selected from the group of methyl, ethyl, fluoromethyl (e.g., $CH_2F$, $CHF_2$, $CF_3$), and fluoroethyl;
—$NHCH_3$;
—$N(CH_3)_2$;
—$N_3$;
—$COOR_{20}$; and
—$NC(O)N(R_{21})(R_{22})$ or —$NC(O)R_{20}$ wherein $R_{20}$ is methyl or ethyl; and $R_{21}$ and $R_{22}$ are independently H, methyl or ethyl.

Among all the compounds of the present invention as disclosed above, preferred are those that can induce caspase activation as determined by the method and under conditions (measurement at 24 hours) described in Example 29, preferably at an $EC_{50}$ of no greater than about 1,000 nM, more preferably at an $EC_{50}$ of no greater than about 500 nM, more preferably at an $EC_{50}$ of no greater than about 200 nM, even more preferably at an $EC_{50}$ of no greater than about 100 nM, and most preferably at an $EC_{50}$ of no greater than about 10 nM. Also preferred compounds are those of Formulae I-VIII, and pharmaceutically acceptable salts or solvates thereof, that are able to inhibit tubulin at an $IC_{50}$ of no greater than about 2,000 nM, preferably no greater than about 1,000 nM, more preferably less than about 500 nM, as determined by the method and under conditions described in Example 31.

Exemplary compounds of the present invention are compounds provided in Examples 1-28, and pharmaceutically acceptable salts or prodrugs thereof, including but not limited to:
Benzo[d][1,2,3]triazin-4-yl-(4-methoxy-phenyl)-methyl-amine;
(4-Methoxyphenyl)-methyl-(6-methylbenzo[d][1,2,3]triazin-4-yl)-amine;
(4-Methoxyphenyl)-methyl-(7-methylbenzo[d][1,2,3]triazin-4-yl)-amine;
(5-Fluoro-benzo[d][1,2,3]triazin-4-yl)-(4-methoxyphenyl)-methyl-amine;
Benzo[d][1,2,3]triazin-4-yl-(3,4-dimethyoxyphenyl)-methyl-amine;
(4-Methoxy-phenyl)-methyl-phthalazin-1-yl-amine;
(4-Chloro-8-fluoro-phthalazin-1-yl)-(4-methoxyphenyl)-methyl-amine;
(4-Chloro-5-fluoro-phthalazin-1-yl)-(4-methoxyphenyl)-methyl-amine;
(4-Chloro-7-methyl-phthalazin-1-yl)-(4-methoxyphenyl)-methyl-amine;
(4-Chloro-6-methyl-phthalazin-1-yl)-(4-methoxyphenyl)-methyl-amine;
(4-Methoxyphenyl)-methyl-(7-methyl-phthalazin-1-yl)-amine;
(4-Methoxyphenyl)-methyl-(6-methyl-phthalazin-1-yl)-amine;
(4-Chlorophthalazin-1-yl)-(3,4-dimethoxyphenyl)-methyl-amine;
(3,4-Dimethoxyphenyl)-methyl-phthalazin-1-yl-amine; and
(5-Fluorophthalazin-1-yl)-(4-methoxyphenyl)-methyl-amine.

Unless specifically stated otherwise or indicated by a bond symbol (dash or double dash), the connecting point to a recited group will be on the right-most stated group. Thus, for example, a hydroxyalkyl group is connected to the main structure through the alkyl and the hydroxyl is a substituent on the alkyl.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include —$NH_2$, —$NHR_x$ and —$NR_xR_y$, wherein $R_x$ and $R_y$ are $C_{1-10}$ alkyl or cycloalkyl groups, or $R_x$ and $R_y$ are combined with the N to form a ring structure, such as a piperidine, or $R_x$ and $R_y$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carboxy or $C_{1-2}$ alkylenedioxy (e.g., methylenedioxy).

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{11}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino(acylamido) groups are any $C_{1-6}$ acyl(alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl(alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon or on a nitrogen atom if the resulting compound is stable, including an oxo substituent ("=O") wherein two hydrogen atoms are replaced.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms.

Useful heteroaryl groups include thienyl(thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl(pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-VIII can be prepared as illustrated by the exemplary reaction in Scheme 1. Reaction of 3H-benzo[d][1,2,3]triazin-4-one with phosphorus oxychloride produced 4-chlorobenzo[d][1,2,3]triazine, which was reacted with a substituted aniline, such as N-methyl-4-methoxy-aniline, to produce the substituted 4-anilino-benzo[d][1,2,3]triazine.

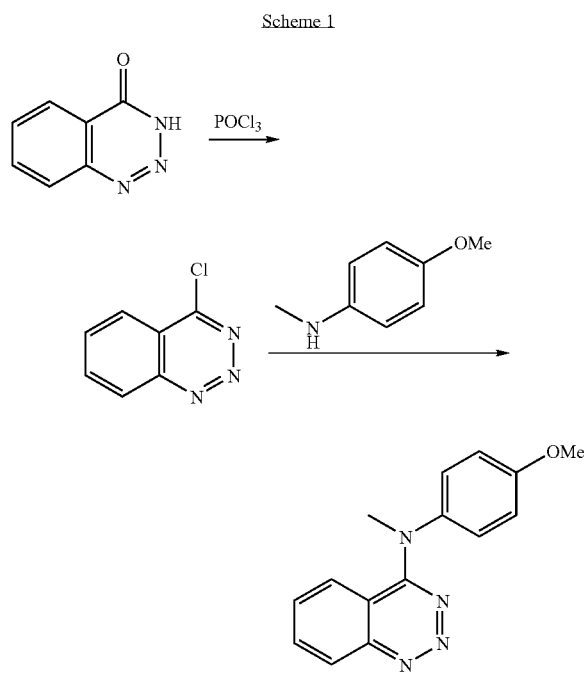

Compounds of this invention with Formulae I-VIII could be prepared as illustrated by the exemplary reaction in Scheme 2. Reaction of 4-chlorobenzo[d][1,2,3]triazine with a substituted aniline, such as 3,4-dimethoxy-aniline, produces the substituted 4-anilino-benzo[d][1,2,3]triazine, which can be methylated by reaction with methyl iodide in the presence of a base such as NaH to produce the N-substituted 4-anilino-benzo[d][1,2,3]triazine.

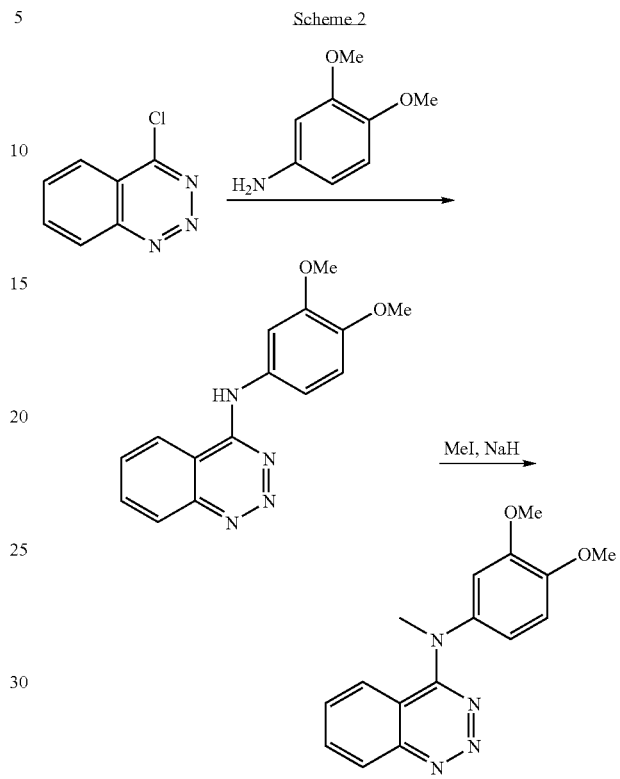

Compounds of this invention with Formulae I-VIII also could be prepared as illustrated by the exemplary reaction in Scheme 3. Reaction of a substituted 2-aminobenzamide, such as 2-amino-5-nitrobenzamide, with $NaNO_2$ in the presence of an acid, such as $H_2SO_4$, produces 6-nitro-3H-benzo[d][1,2,3]triazin-4-one, which is converted to 4-chloro-6-nitrobenzo[d][1,2,3]triazine by reaction with phosphorus oxychloride. Reaction of 4-chloro-6-nitrobenzo[d][1,2,3]triazine with a substituted aniline, such as N-methyl-4-methoxy-aniline, produces the substituted 4-anilino-6-nitrobenzo[d][1,2,3]triazine, and the nitro group can be reduced via hydrogenation to produce the substituted 6-amino-4-anilino-benzo[d][1,2,3]triazine.

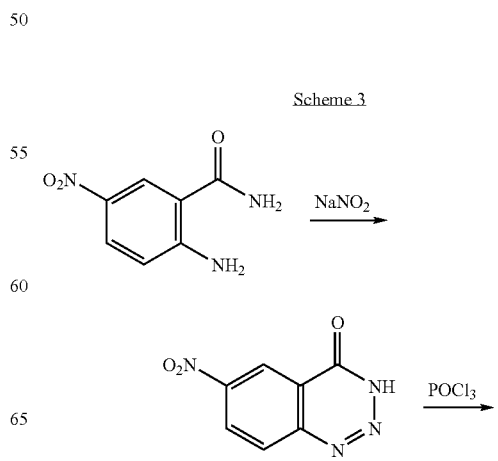

-continued

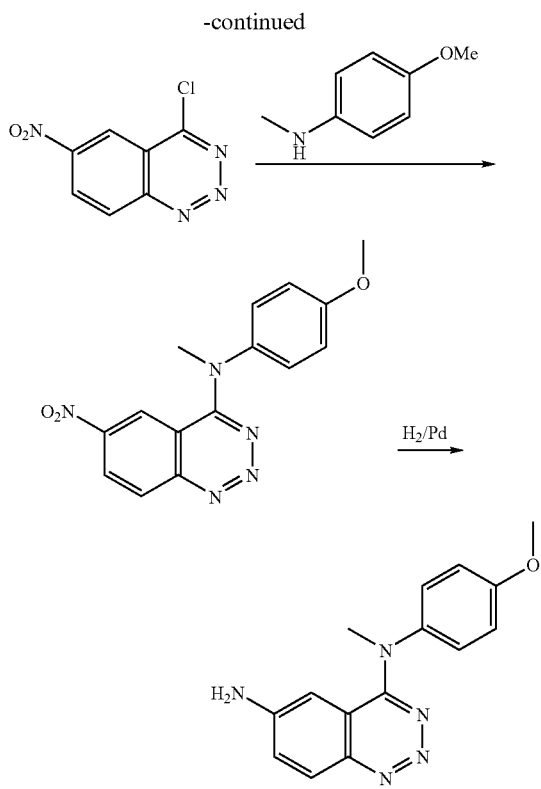

Alternatively, compounds of this invention with Formulae I-VIII also could be prepared as illustrated by the exemplary reaction in Scheme 4. Reaction of 4-chlorobenzo[d][1,2,3]triazine with a substituted aniline, such as N-methyl-4-nitro-aniline, produces the substituted 4-anilino-benzo[d][1,2,3]triazine. The nitro group can be reduced via hydrogenation to produce the substituted 4-(4-amino-anilino)-benzo[d][1,2,3]triazine, which can react with an acyl chloride, such as acetyl chloride, to produce the substituted 4-(4-acetylamino-anilino)-benzo[d][1,2,3]triazine.

Scheme 4

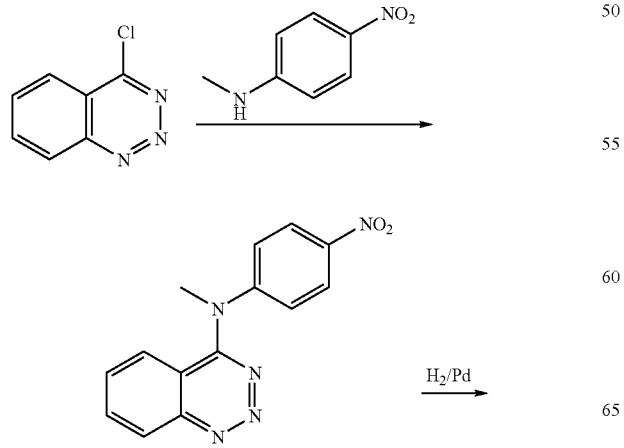

-continued

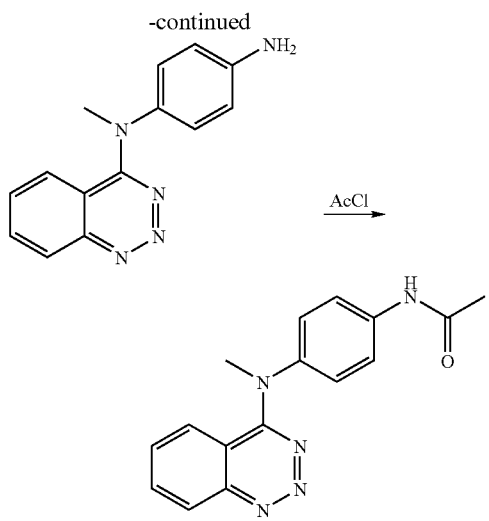

Compounds of this invention with Formulae I-VIII also could be prepared as illustrated by the exemplary reaction in Scheme 5. Reaction of 2-aminopyridine-3-carboxamide with NaNO$_2$ in the presence of an acid, such as H$_2$SO$_4$, produces pyrido[2,3-d][1,2,3]triazin-4(3H)-one, which is converted to 4-chloropyrido[2,3-d][1,2,3]triazine by reaction with phosphorus oxychloride. Reaction of 4-chloropyrido[2,3-d][1,2,3]triazine with a substituted aniline, such as N-methyl-4-methoxy-aniline, produces the substituted 4-anilino-pyrido[2,3-d][1,2,3]triazine.

Scheme 5

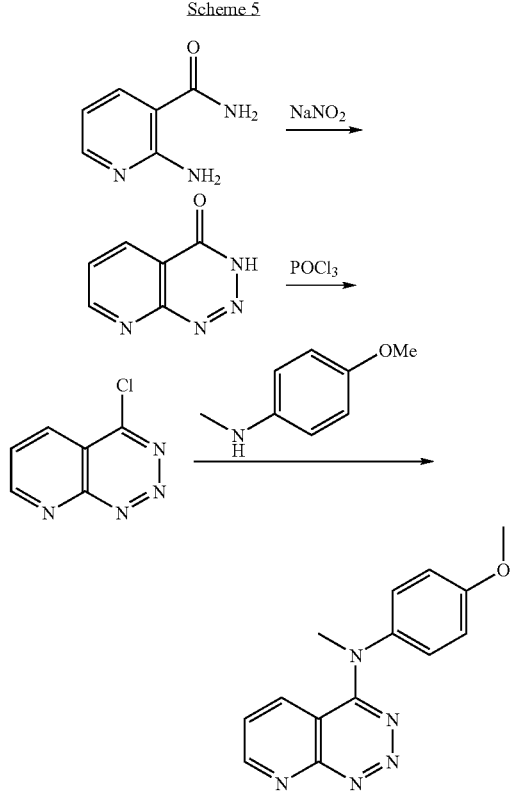

Compounds of this invention with Formulae I-VIII also could be prepared as illustrated by the exemplary reaction in Scheme 6. Reaction of phthalazin-1(2H)-one with phosphorus oxychloride produced 1-chlorophthalazine, which was reacted with a substituted aniline, such as N-methyl-4-methoxy-aniline, to produce the substituted 1-anilino-phthalazine.

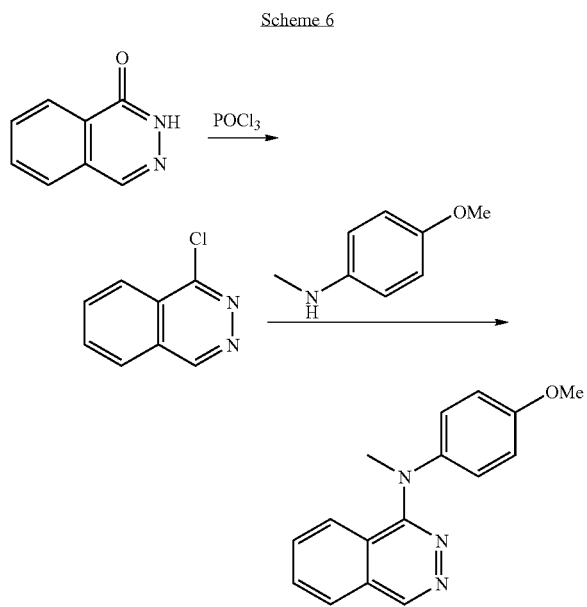

Compounds of this invention with Formulae I-VIII could be prepared as illustrated by the exemplary reaction in Scheme 7. Reaction of 1-chlorophthalazine with a substituted aniline, such as 3,4-dimethoxy-aniline, produces the substituted 1-anilino-phthalazine, which may be methylated by reaction with methyl iodide in the presence of a base such as NaH to produce the N-substituted 1-anilino-phthalazine.

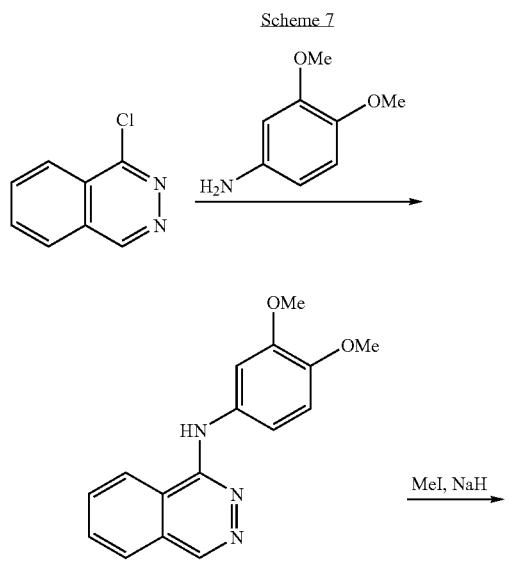

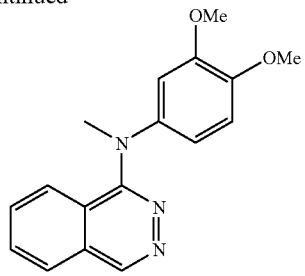

Alternatively, compounds of this invention with Formulae I-VIII also could be prepared as illustrated by the exemplary reaction in Scheme 8. Reaction of 1-chlorophthalazine with a substituted aniline, such as N-methyl-4-nitro-aniline, produces the substituted 1-anilino-phthalazine. The nitro group can be reduced via hydrogenation to produce the substituted 1-(4-amino-anilino)-phthalazine, which can react with an acyl chloride, such as acetyl chloride, to produce the substituted 1-(4-acetylamino-anilino)-phthalazine.

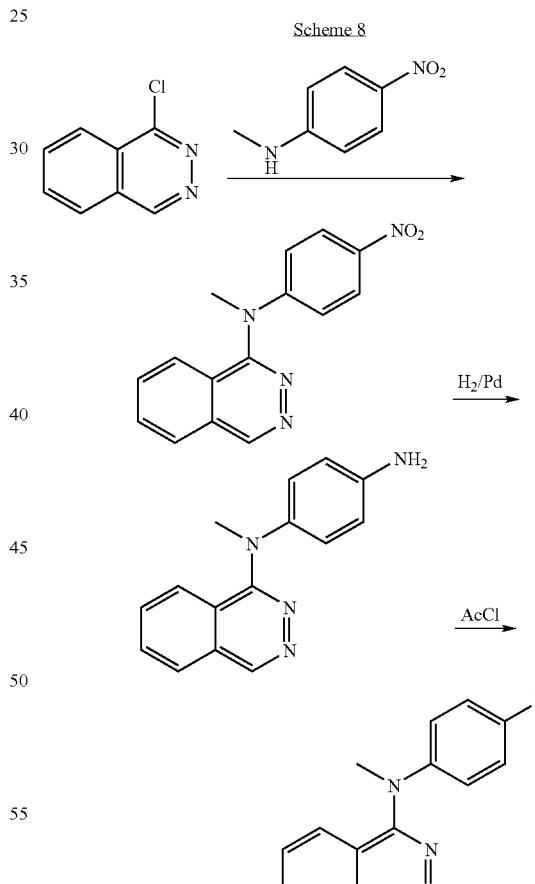

Compounds of this invention with Formulae I-VIII also could be prepared as illustrated by the exemplary reaction in Scheme 9. Reaction of a substituted 2-formylbenzoic acid, such as 6-formyl-2,3-dimethoxybenzoic acid, with $NH_2NH_2$ produces 7,8-dimethoxy-phthalazin-1(2H)-one, which is converted to 1-chloro-7,8-dimethoxy-phthalazine by reaction with phosphorus oxychloride. Reaction of 1-chloro-7,8- dimethoxy-phthalazine with a substituted aniline, such as N-methyl-4-methoxy-aniline, produces the substituted 1-anilino-7,8-dimethoxy-phthalazine.

Scheme 9

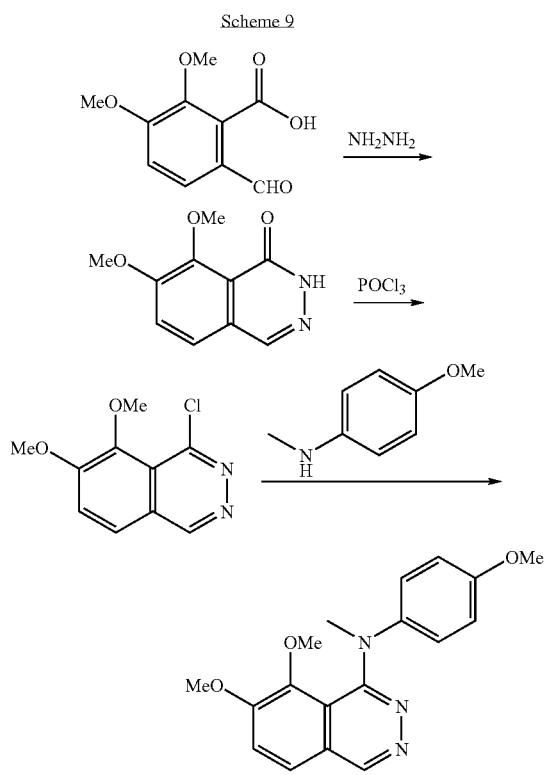

Compounds of this invention with Formulae I-VIII can be prepared as illustrated by the exemplary reaction in Scheme 10. Diazotization of 2'-aminoacetophenone by $NaNO_2$ in an acidic solution, such as $H_2SO_4/CH_3CO_2H/H_2O$, followed by decomposition of the diazonium salt produces the cinnolinone, which is converted to 4-chloro-cinnoline by reaction with a chlorination agent, such as thionyl chloride (Hennequin et al. *J. Med. Chem.* 1999, 42, 5369-5389). Reaction of 4-chloro-cinnoline with a substituted aniline, such as N-methyl-4-methoxy-aniline, produces the N-substituted 4-anilino-cinnoline.

Scheme 10

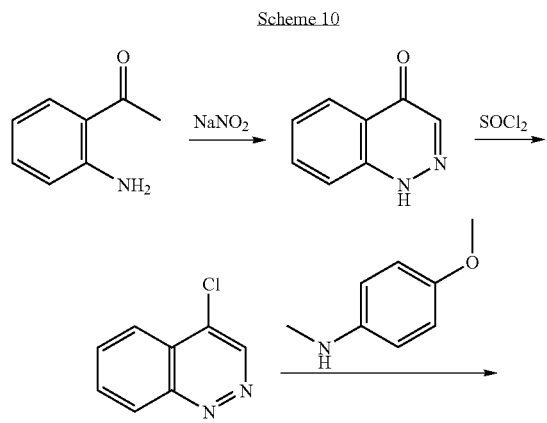

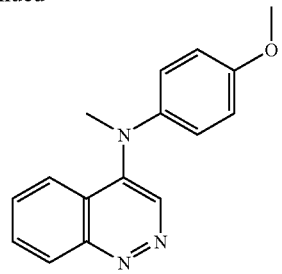

Compounds of this invention with Formulae I-VIII can be prepared as illustrated by the exemplary reaction in Scheme 11. Reaction of 4-chloro-cinnoline with a substituted aniline, such as 3,4-dimethoxy-aniline, produces the substituted 4-anilino-cinnoline, which can be methylated by reaction with methyl iodide in the presence of a base such as NaH to produce the N-substituted 4-anilino-cinnoline.

Scheme 11

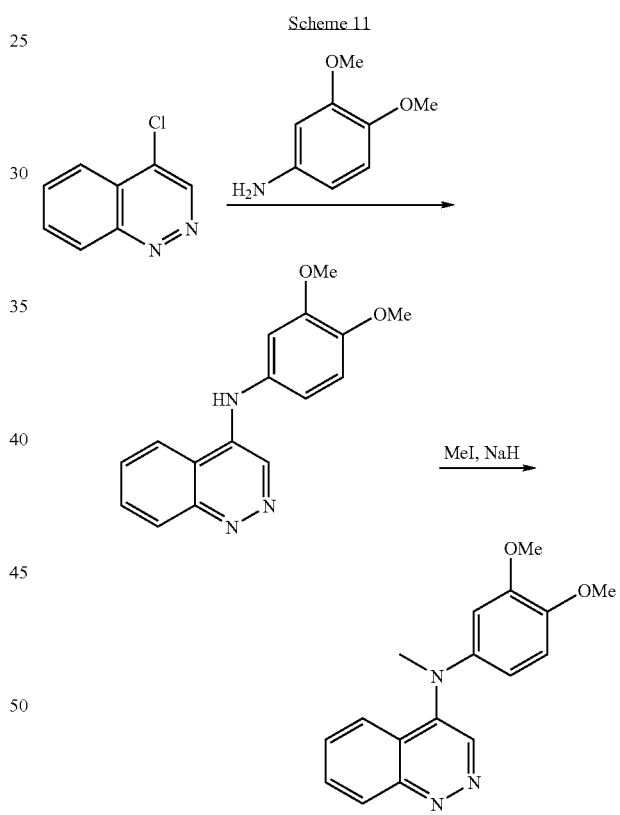

Compounds of this invention with Formulae I-VIII also can be prepared as illustrated by the exemplary reaction in Scheme 12. Reaction of 2-amino-3-acetylpyridine, with $NaNO_2$ in an acidic solution, such as $H_2SO_4/CH_3CO_2H/H_2O$, followed by decomposition of the diazonium salt produces pyrido[2,3-c]pyridazin-4(1H)-one, which is converted to 4-chloropyrido[2,3-c]pyridazine by reaction with a chlorination agent, such as thionyl chloride. Reaction of 4-chloropyrido[2,3-c]pyridazine with a substituted aniline, such as N-methyl-4-methoxy-aniline, produces the N-substituted 4-anilino-pyrido[2,3-c]pyridazine.

Scheme 12

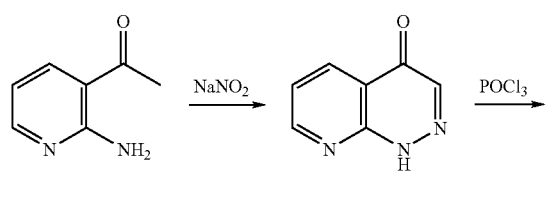

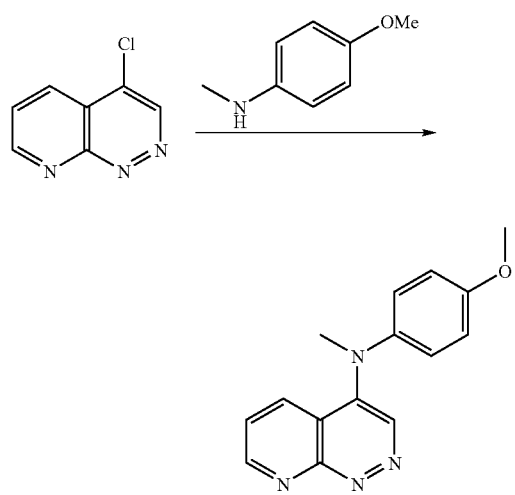

Compounds of this invention with Formulae I-VIII also can be prepared as illustrated by the exemplary reaction in Scheme 13. Reaction of 2-acetyl-3-amino-pyridine, with NaNO$_2$ in an acidic solution, such as H$_2$SO$_4$/CH$_3$CO$_2$H/H$_2$O, followed by decomposition of the diazonium salt produces pyrido[3,2-c]pyridazin-4(1H)-one, which is converted to 4-chloropyrido[3,2-c]pyridazine by reaction with a chlorination agent, such as thionyl chloride. Reaction of 4-chloropyrido[3,2-c]pyridazine with a substituted aniline, such as N-methyl-4-methoxy-aniline, produces the N-substituted 4-anilino-pyrido[3,2-c]pyridazine.

Scheme 13

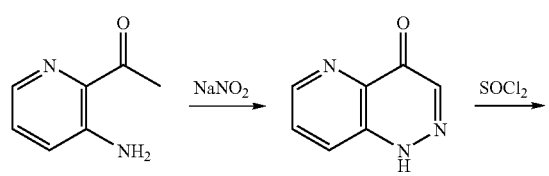

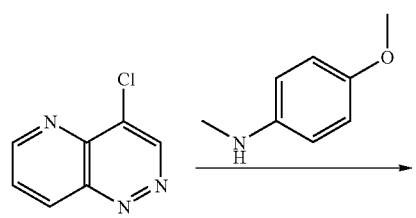

Alternatively, compounds of this invention with Formulae I-VIII also could be prepared as illustrated by the exemplary reaction in Scheme 14. Reaction of 4-chloro-cinnoline with a substituted aniline, such as N-methyl-4-nitro-aniline, produces the substituted 4-anilino-cinnoline. The nitro group can be reduced via hydrogenation to produce the substituted 4-(4-amino-anilino)-cinnoline, which can react with an acyl chloride, such as acetyl chloride, to produce the substituted 4-(4-acetylamino-anilino)-cinnoline.

Scheme 14

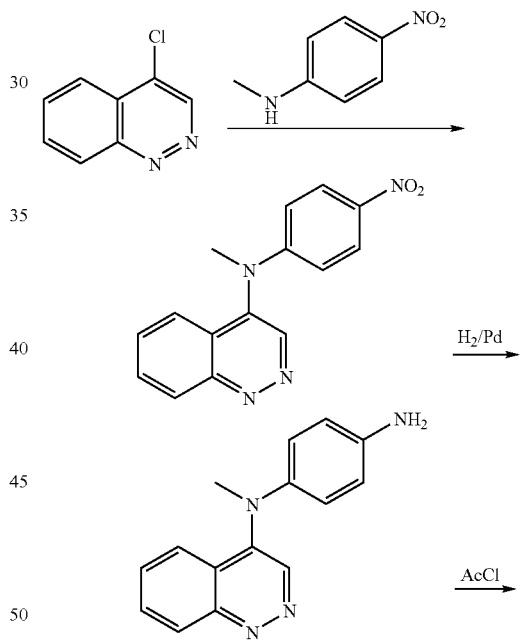

Compounds of this invention with Formulae I-VIII also can be prepared as illustrated by the exemplary reaction in Scheme 15. Reaction of 4-bromo-isoquinoline with a substituted aniline, such as N-methyl-4-methoxy-aniline, in the presence of Pd$_2$(dba)$_3$ and BINAP, and a base such as MeONa (Prashad et al. *J. Org. Chem.* 2000, 65, 2612-2614), produces the N-substituted 4-anilino-isoquinoline.

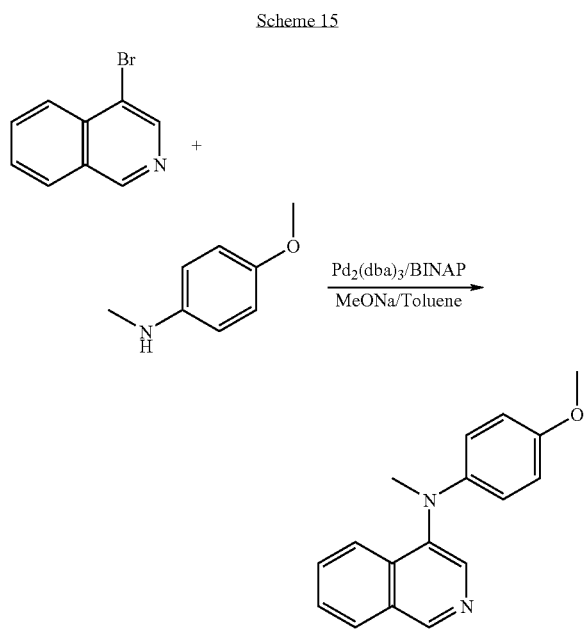

Compounds of this invention with Formulae I-VIII can be prepared as illustrated by the exemplary reaction in Scheme 16. Reaction of 4-bromo-isoquinoline with a substituted aniline, such as 3,4-dimethoxy-aniline, in the presence of $Pd_2(dba)_3$ and BINAP, and a base such as MeONa, produces the substituted 4-anilino-isoquinoline, which can be methylated by reaction with methyl iodide in the presence of a base such as NaH to produce the N-substituted 4-anilino-isoquinoline.

Alternatively, compounds of this invention with Formulae I-VIII also can be prepared as illustrated by the exemplary reaction in Scheme 17. Reaction of 4-chloroisoquinoline with a substituted aniline, such as N-methyl-4-nitro-aniline, in the presence of $Pd_2(dba)_3$ and BINAP, and a base such as MeONa, produces the substituted 4-anilino-isoquinoline. The nitro group can be reduced via hydrogenation to produce the substituted 1-(4-amino-anilino)-isoquinoline, which can react with an acyl chloride, such as acetyl chloride, to produce the substituted 1-(4-acetylamino-anilino)-isoquinoline.

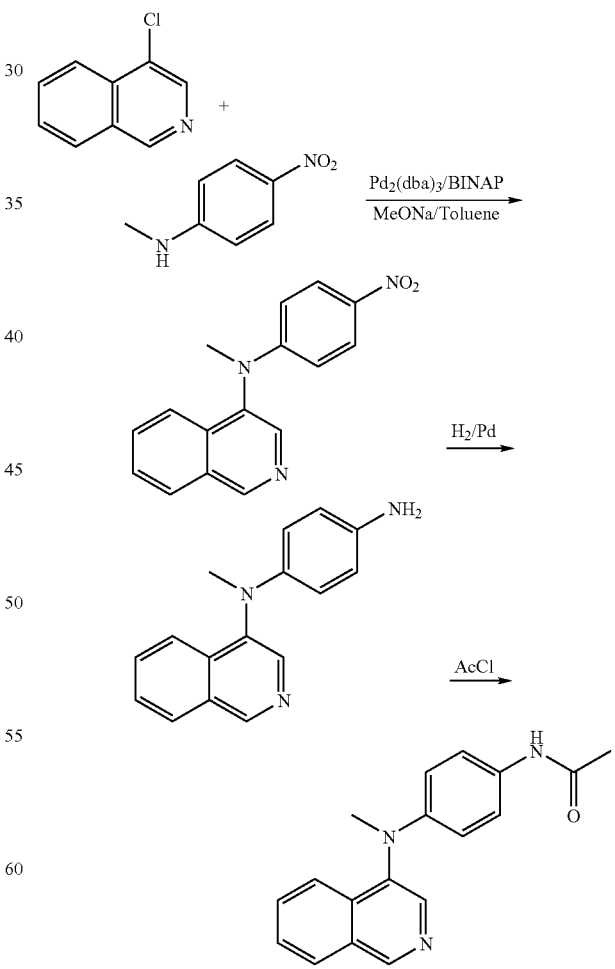

Compounds of this invention with Formulae I-VIII also can be prepared as illustrated by the exemplary reaction in Scheme 18. Reaction of 8-bromo-1,6-naphthyridine with a substituted aniline, such as N-methyl-4-methoxy-aniline, in the presence of Pd$_2$(dba)$_3$ and BINAP, and a base such as MeONa, produces the substituted 8-anilino-1,6-naphthyridine.

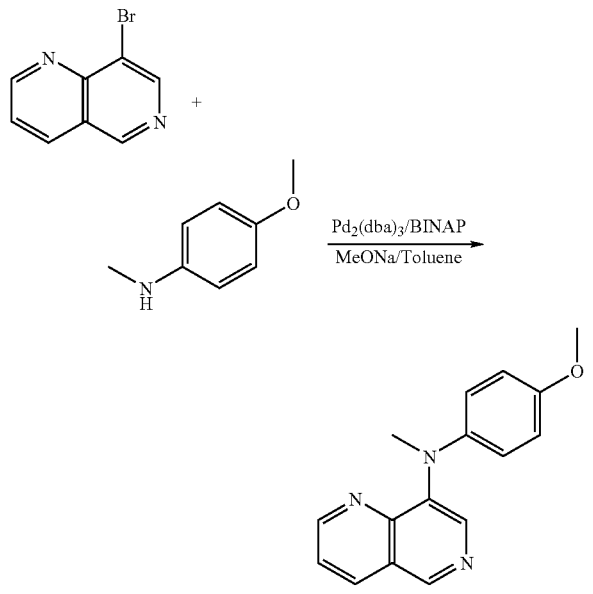

Compounds of this invention with Formulae I-VIII could be prepared as illustrated by the exemplary reaction in Scheme 19. Reaction of an optionally substituted 2-aminobenzamide, such as 2-amino-5-methylbenzamide, with NaNO$_2$ under acidic conditions, such as 2 N HCl, followed by treatment with a base, such as Na$_2$CO$_3$, produces an optionally substituted 3H-benzo[d][1,2,3]triazin-4-one, such as 7-methyl-3H-benzo[d][1,2,3]triazin-4-one. Exposure of the optionally substituted 3H-benzo[d][1,2,3]triazin-4-one, such as 7-methyl-3H-benzo[d][1,2,3]triazin-4-one, to a coupling agent, such as PyBOP, in the presence of a base and an amine, such as N-methyl-p-anisidine, provides the substituted triazine.

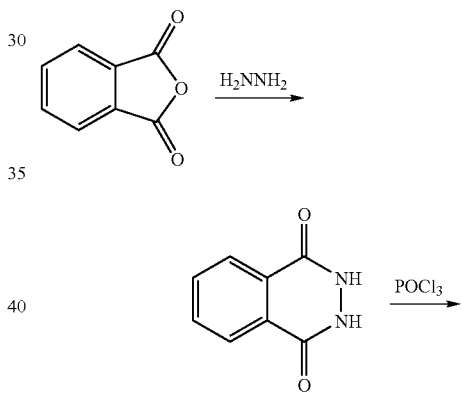

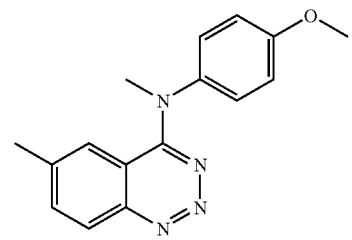

Compounds of this invention with Formulae I-VIII could be prepared as illustrated by the exemplary reaction in Scheme 20. Reaction of phthalic anhydride with hydrazine hydrate in acetic acid produces 2,3-dihydro-phthalazine-1,4-dione. Chlorination of 2,3-dihydro-phthalazine-1,4-dione and subsequent reaction with an amine, such as N-methyl-p-anisidine, produces the substituted 4-chlorophthalazine, such as (4-chlorophthalazin-1-yl)(4-methoxyphenyl)-amine. The chloro group can then be removed via hydrogenation to produce the substituted phthalazine, such as (4-methoxyphenyl)-methylphthalazin-1-yl-amine.

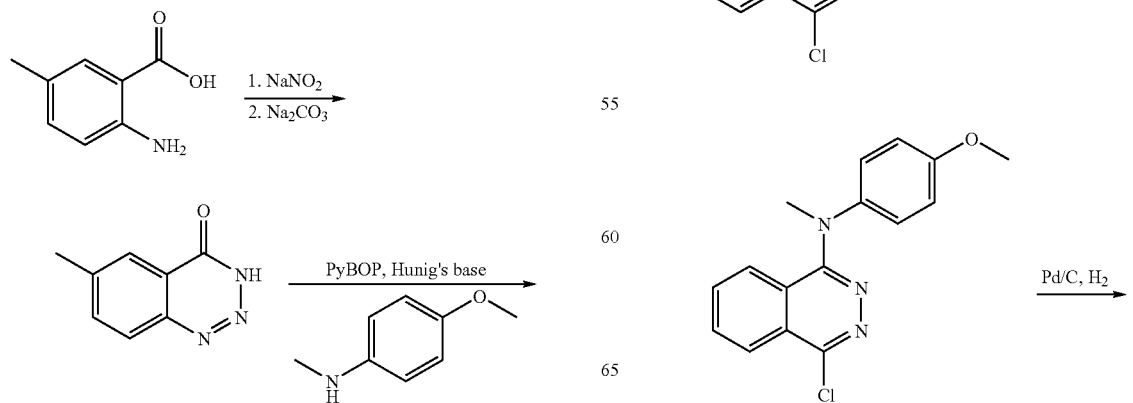

-continued

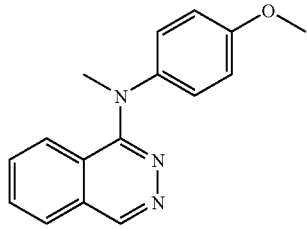

An important aspect of the present invention is the discovery that compounds having Formulae I-VIII are activators of caspases and inducers of apoptosis. Another important aspect of the invention is that compounds having Formulae I-VIII are inhibitors of tubulin polymerization. Therefore, these compounds are useful in treating diseases that are responsive to activating caspases, inducing apoptosis, or inhibiting tubulin. For example, these compounds are useful in a variety of clinical conditions in which there is uncontrolled cell growth and spread of abnormal cells, such as in the case of cancer.

The present invention also includes a therapeutic method comprising administering to an animal an effective amount of a compound, or a pharmaceutically acceptable salt or prodrug of said compound of Formulae I-VIII, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

Another aspect of the present invention is to provide a pharmaceutical composition, containing an effective amount of a compound of Formulae I-VIII, or a pharmaceutically acceptable salt of said compound, in admixture with one or more pharmaceutically acceptable carriers or diluents.

In one embodiment, a pharmaceutical composition comprising a compound of Formulae I-VIII disclosed herein, or a pharmaceutically acceptable salt of said compound, in combination with a pharmaceutically acceptable vehicle is provided.

Preferred pharmaceutical compositions comprise compounds of Formulae I-VIII, and pharmaceutically acceptable salts, esters, or prodrugs thereof, that are able to induce caspase activation as determined by the method described in Example 31, preferably at an $EC_{50}$ no greater than 1,000 nM, more preferably at an $EC_{50}$ no greater than 500 nM, more preferably at an $EC_{50}$ no greater than 200 nM, more preferably at an $EC_{50}$ no greater than 100, and most preferably at an $EC_{50}$ no greater than 10 nM. Other preferred compositions comprise compounds of Formulae I-VIII, and pharmaceutically acceptable salts, esters, or prodrugs thereof, that are able to inhibit tubulin polymerization as determined by the method described in Example 33.

Another embodiment of the present invention is directed to a composition effective to inhibit neoplasia comprising a compound, or a pharmaceutically acceptable salt or prodrug of said compound of Formulae I-VIII, which functions as a caspase cascade activator and inducer of apoptosis or inhibitor of tubulin polymerization, in combination with at least one known cancer chemotherapeutic agent, or a pharmaceutically acceptable salt of said agent. Examples of known cancer chemotherapeutic agents which may be used for combination therapy include, but are not limited to alkylating agents, such as busulfan, cisplatin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab). Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., *Cancer Res* 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known alpha-1-adrenoceptor antagonist, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., *Cancer Res.* 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res.* 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., *Nat. Med.* 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as ST1571 (Gleevec® (imatinib mesylate)), have potent synergetic effect in combination with other anti-leukemic agents, such as etoposide (Liu, W. M., et al. *Br. J. Cancer* 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known tyrosine kinase inhibitor, or a pharmaceutically acceptable salt of said agent. Examples of known tyrosine kinase inhibitors, which can be used for combination therapy include, but are not limited to, Gleevec® (imatinib mesylate), ZD1839 Iressa® (gefitinib), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., *Clin. Cancer Res.* 7:3544-3550 (2001)). Synergy of the protein farnesyltransferase inhibitor $SCH_{66336}$ and cisplatin in human cancer cell lines also has been reported (Adjei, A. A., et al., *Clin. Cancer. Res.* 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known cyclin-dependent kinase inhibitor, or a pharmaceutically acceptable salt of said agent. Examples of known cyclin-dependent kinase inhibitors, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16(No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis or inhibitor of tubulin polymerization, in bioconjugation with at least one known therapeutically useful antibody, such as Herceptin® (trastuzumab) or Rituxan® (rituximab), growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® (trastuzumab) or Rituxan® (rituximab).

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis or inhibitor of tubulin polymerization. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-VIII, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgarism Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-VIII, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although $R^A$ synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-VIII, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-VIII, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiecence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers are useful as therapeutics for HIV, HCV, HBV, and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Another important aspect of the present invention is that compounds of the present invention are potent and highly efficacious activators of caspase-3 and inhibitors of tubulin polymerization even in drug resistant cancer cells, which enables these compounds to inhibit the growth and proliferation of drug resistant cancer cells, and to cause apoptosis and cell death in the drug resistant cancer cells. Specifically, the compounds of the present invention are not substrates for the MDR transporters such as Pgp-1 (MDR-1), MRP-1 and BCRP. This is particularly surprising in view of the fact that almost all of the commercially available tubulin-interacting chemotherapeutics are substrates for multidrug resistance transporters (MDRs).

Multidrug resistance is the major cause of chemotherapy failure. Drug resistance is typically caused by ATP-dependent efflux of drug from cells by ATP-binding cassette (ABC) transporters. In particular, the ABC transporters ABCB1 (MDR-1, P glycoprotein); ABCC1 (MRP1); and ABCG2 (BCRP, MXR) are typically over-expressed in drug resistant tumors and thus are implicated in drug resistance. In comparison to most standard anti-cancer drugs, which are not effective in killing drug resistant cancer cells, the compounds of the present invention are effective in killing drug resistant cancer cells. Therefore, compounds of this invention are useful for the treatment of drug resistant cancer.

Thus, another aspect of the present invention is the application of the methods and compounds of the present invention as described above to tumors that have acquired resistance to other anticancer drugs. In one embodiment, a compound of the present invention is administered to a cancer patient who has been treated with another anti-cancer drug. In another embodiment, a compound of the present invention is administered to a patient who has been treated with and is not responsive to another anti-cancer drug or developed resistance to such other anti-cancer compound. In another embodiment, a compound of the present invention is administered to a patient who has been treated with another anti-cancer drug and is refractory to said other anti-cancer drug. The compounds of the present invention can be used in treating cancer in a patient who is not responsive or is resistant to any other anti-cancer agent. Examples of such other anti-cancer agent may include alkylating agents, antimitotic agents, topo I inhibitors, topo II inhibitors, RNA/DNA antimetabolites, EGFR inhibitors, angiogenesis inhibitors, tubulin inhibitors (e.g., vinblastine, taxol® (paclitaxel), and analogues thereof), proteosome inhibitors, etc., some of the exemplary compounds of which are provided above and are general known in the art, e.g., melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. The compounds can be used in treating patients having any type of diseases responsive to the inhibition of tubulin (including but not limited to the types of cancer described above) who are not responsive or become resistant to another therapeutic agent, e.g., another anti-cancer agent.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

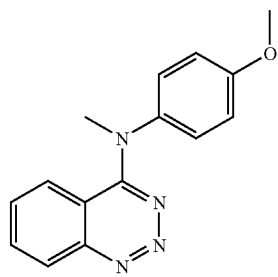

Benzo[d][1,2,3]triazin-4-yl-(4-methoxy-phenyl)-methyl-amine

To a suspension of 3H-Benzo[d][1,2,3]triazin-4-one (0.502 g, 3.4 mmol) in toluene (5 mL) was added diisopropyl ethyl amine (1.2 mL, 6.9 mmol) and phosphorus oxychloride (0.5 mL, 5.4 mmol) at −78° C. under argon. The reaction mixture was stirred at room temperature for 75 min, then diluted with EtOAc (50 mL) and washed with water (15 mL). The aqueous layer was extracted with EtOAc (2×50 mL). The EtOAc solutions were combined, washed with saturated $NaHCO_3$ (15 mL), dried, and evaporated to give a brown solid.

The above crude product was stirred with N-methyl-4-methoxy-aniline (138 mg, 1 mmol) in isopropanol (10 mL) at room temperature for 26 h. The solvent was evaporated and the residue was stirred with EtOAc (50 mL) and saturated $Na_2CO_3$ (15 mL). The EtOAc layer was separated, washed with 1M citric acid (10 mL), dried with $MgSO_4$, and evaporated. The brown residue was purified by column chromatography ($SiO_2$, EtOAc:hexanes/10-50%) to give a light brown solid. The solid was suspended in a small amount of EtOAc and was stirred overnight. The off-white product was collected by filtration (37 mg, 4%): $^1$H NMR ($CDCl_3$) 8.19 (dd, J=0.6, 8.1 Hz, 1H), 7.76 (m, 1H), 7.33 (m, 1H), 7.20-7.16 (m, 2H), 7.00-6.95 (m, 2H), 6.87 (dd, J=0.6, 9.3 Hz, 1H), 3.87 (s, 3H), 3.75 (s, 3H).

EXAMPLE 2

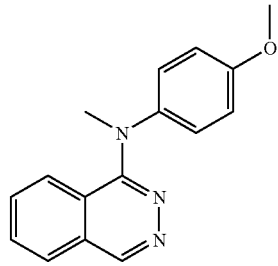

(4-Methoxy-phenyl)-methyl-phthalazin-1-yl-amine

A solution of 2H-Phthalazin-1-one (1.01 g, 5 mmol) in phosphorus oxychloride (5 mL) was stirred at 130° C. for 1.5 h. The phosphorus oxychloride was removed under reduced pressure. The residue was partitioned between water (10 mL) and methylene chloride (50 mL). The methylene chloride phase was separated, dried over MgSO$_4$, and evaporated to give a yellow solid (1.015 g, 90%).

The above crude product (83 mg, 0.50 mmol), N-methyl-4-methoxy-aniline (69 mg, 0.50 mmol) and cesium carbonate (200 mg, 0.61 mmol) were stirred in anhydrous DMF (1 mL) in a sealed tube at rt for 17 h. The reaction was diluted with water (5 mL) and extracted with EtOAc (2×20 mL). The EtOAc solution was washed with water (5 mL), dried, and evaporated to give a brown residue. The crude product was purified by column chromatography (SiO$_2$, EtOAc:hexanes/ 15-50%) to give a light yellow solid (5 mg, 4%): $^1$H NMR (CDCl$_3$) 9.11 (s, 1 H), 7.85 (m, 1 H), 7.66 (m, 1 H), 7.48-7.47 (m, 2 H), 7.40-7.10 (m, 2 H), 6.87-6.81 (m, 1 H), 3.80 (s, 3 H), 3.63 (s, 3 H).

EXAMPLE 3

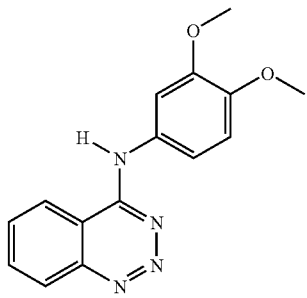

Benzo[d][1,2,3]triazin-4-yl-(3,4-dimethoxyphenyl)-amine

Benzo[d][1,2,3]triazin-4-yl-(3,4-dimethoxyphenyl)-amine was synthesized using a procedure similar to (4-methoxyphenyl)-methyl-(6-methylbenzo[d][1,2,3]triazin-4-yl)-amine. $^1$H NMR (DMSO-d$_6$) δ 9.84 (br s, 1 H), 8.58 (d, 1 H), 8.18 (dd, 1 H), 8.12 (td, 1 H), 7.96-8.04 (m, 1 H), 7.36-7.54 (m, 2 H), 7.04 (d, 1 H), 3.80 (s, 3 H), 3.79 (s, 3 H). MS (ES) 281 (M−H), 283 (M+H).

EXAMPLE 4

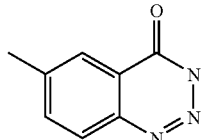

6-Methyl-3H-benzo[d][1,2,3]triazin-4-one

A suspension of 2-amino-5-methylbenzamide (500 mg, 3.3 mmol) in HCl (2N, 5 mL) at 0° C. was treated with NaNO$_2$ (252 mg, 3.7 mmol) for 1.25 h. The suspension was then filtered. The filtrate was made basic with Na$_2$CO$_3$ (20% soln) and the resulting solid collected via vacuum filtration to provide 334.7 mg (63%) of the title compound as a white solid. $^1$H NMR (DMSO-d$_6$) δ 8.06-8.11 (m, 1 H), 8.05 (d, 1 H), 7.87-7.91 (m, 1 H) 2.59 (s, 3 H). HRMS (ES) calcd for C$_8$H$_8$N$_3$O (M+H) 162.0662, found 162.0660.

EXAMPLE 5

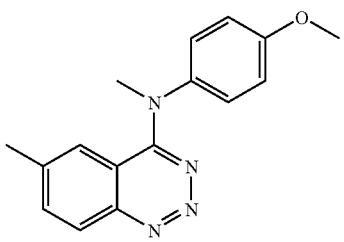

(4-Methoxyphenyl)-methyl-(6-methylbenzo[d][1,2,3]triazin-4-yl)-amine

Benzotriazol-1-yloxytris(pyrrolidino)phosphonium hexafluorophosphate (PyBOP, 603.2 mg, 1.16 mmol) was added to a solution of methyl-3H-benzo[d][1,2,3]triazin-4-one (168.7 mg, 1.05 mmol), Hünig's base (0.45 mL, 2.58 mmol) and N-methyl-p-anisidine (148.2 mg, 1.08 mmol) in DMF (2 mL). The mixture was then stirred for 4 hours at rt. The reaction was diluted with EtOAc and washed with H$_2$O. The aqueous layer was extracted once with EtOAc. The combined organic layers were dried (MgSO$_4$), filtered and concentrated. The residue was purified via 2 gradient MPLC columns (SiO$_2$, 0 to 100%, EtOAc/hexanes, 30 min) to provide 71.7 mg (24%) of the title compound. $^1$H NMR (DMSO-d$_6$) δ 8.04 (d, 1 H), 7.74 (ddd, 1 H), 7.28-7.36 (m, 2 H), 7.03-7.09 (m, 2 H), 6.40-6.50 (m, 1 H), 3.81 (s, 3 H), 3.63 (s, 3 H), 2.15 (s, 3 H). MS (ES) 281 (M+H).

EXAMPLE 6

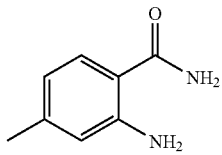

2-Amino-4-methylbenzamide

Concentrated sulfuric acid (3 mL) was carefully added to a suspension of 2-amino-4-methylbenzonitrile (800 mg, 6.1 mmol) in H$_2$O (1 mL). The solution was then placed into an oil bath, pre-heated to 120° C., the reaction stirred for 20 min and then immediately cooled in an ice bath. The solution was made basic via the addition of 5% NaOH and the resulting solid collected via vacuum filtration. 484.4 mg (53%) of the title compound as a light brown solid were obtained. $^1$H NMR (DMSO-$d_6$) δ 7.63 (br s, 1 H), 7.42 (d, 1 H), 6.95 (br s, 1 H), 6.55 (br s, 2 H), 6.45-6.48 (m, 1 H), 6.29 (ddd, 1 H), 2.16 (s, 3 H). MS (ES) 134 (M−16).

EXAMPLE 7

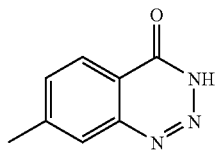

7-Methyl-3H-benzo[d][1,2,3]triazin-4-one

A suspension of 2-amino-5-methylbenzamide (404 mg, 2.7 mmol) in HCl (2N, 5 mL) at 0° C. was treated with NaNO$_2$ (208 mg, 3.0 mmol). The mixture was stirred for 1 h, then made basic with Na$_2$CO$_3$ (20% soln). The resulting solid was collected via vacuum filtration to provide 249 mg (57%) of the title compound as a brown solid. $^1$H NMR (DMSO-$d_6$) δ 8.11 (d, 1 H), 7.96-8.00 (m, 1 H), 7.73 (ddd, 1 H), 2.56 (s, 3 H). MS (ES) 160 (M−H), 162 (M+H).

EXAMPLE 8

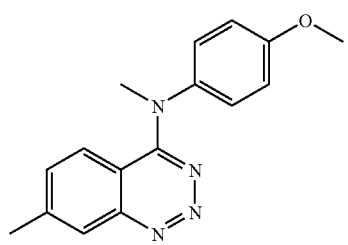

(4-Methoxyphenyl)-methyl-(7-methylbenzo[d][1,2,3]triazin-4-yl)-amine (4-Methoxyphenyl)-methyl-(7-methylbenzo[d][1,2,3]triazin-4-yl)-amine was synthesized using a procedure similar to (4-methoxyphenyl)-methyl-(6-methylbenzo[d][1,2,3]triazin-4-yl)-amine. The title compound was isolated in 32% yield. $^1$H NMR (DMSO-$d_6$) δ 7.90-7.95 (m, 1 H), 7.28-7.38 (m, 3 H), 7.00-7.08 (m, 2 H), 6.70 (d, 1 H), 3.80 (s, 3 H), 3.62 (s, 3 H), 2.45 (s, 3 H). $^{13}$C NMR (DMSO-$d_6$) δ 159.0, 153.8, 145.5, 144.9, 140.2, 133.1, 128.3, 127.0, 124.4, 116.2, 108.3, 56.1, 42.9, 21.8. MS (ES) 281 (M+H).

EXAMPLE 9

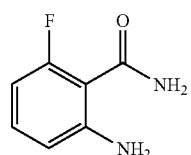

2-Amino-6-fluorobenzamide

2-Amino-6-fluorobenzamide was synthesized using a procedure similar to 2-amino-4-methylbenzamide. The title compound was isolated in 31% yield as a white solid, along with residual starting material (17% by weight). $^1$H NMR (DMSO-$d_6$) δ 7.55 (br s, 1H), 7.51 (br s, 1 H), 7.07 (td, 1 H), 6.50 (ddd, 1 H), 6.30 (ddd, 1 H), 6.16 (br s, 2 H). MS (ES) 138 (M−16).

EXAMPLE 10

5-Fluoro-3H-benzo[d][1,2,3]triazin-4-one

NaNO$_2$ (139.7 mg, 2.02 mmol) was added to a suspension of 2-amino-6-fluorobenzamide (~282 mg, 1.8 mmol) and 2-amino-6-fluorobenzonitrile (~46 mg, 0.34 mmol) in HCl (2 N, 5 mL) at 0° C. The mixture was stirred for 1 h. Na$_2$CO$_3$ (20% soln) was added until the solution was basic and the resulting solid removed via vacuum filtration. The filtrate was then acidified with HCl (2 N) and the precipitate collected via vacuum filtration to provide 178.5 mg (64%) of the title compound. $^1$H NMR (DMSO-$d_6$) δ 8.08 (td, 1 H), 8.05-7.97 (m, 1 H), 7.70 (ddd, 1 H). MS (ES) 164 (M−H), 166 (M+H).

EXAMPLE 11

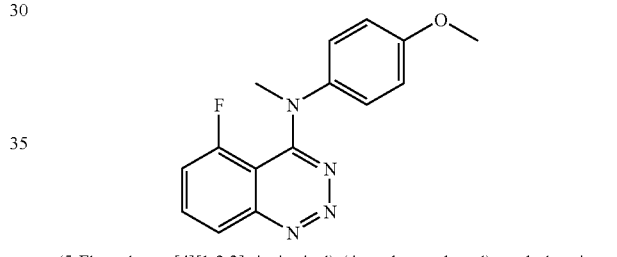

(5-Fluorobenzo[d][1,2,3]triazin-4-yl)-(4-methoxy-phenyl)-methyl-amine (5-Fluoro-benzo[d][1,2,3]triazin-4-yl)-(4-methoxyphenyl)-methylamine was synthesized using a procedure similar to (4-methoxyphenyl)-methyl-(6-methylbenzo[d][1,2,3]triazin-4-yl)-amine. The title compound was isolated in 15% yield. $^1$H NMR (DMSO-$d_6$) δ 8.03 (dd, 1 H), 7.97 (td, 1 H), 7.42 (ddd, 1 H), 7.07-7.14 (m, 2 H), 6.83-6.95 (m, 2 H), 3.73 (s, 3 H), 3.65 (s, 3 H). MS (ES) 285 (M+H).

EXAMPLE 12

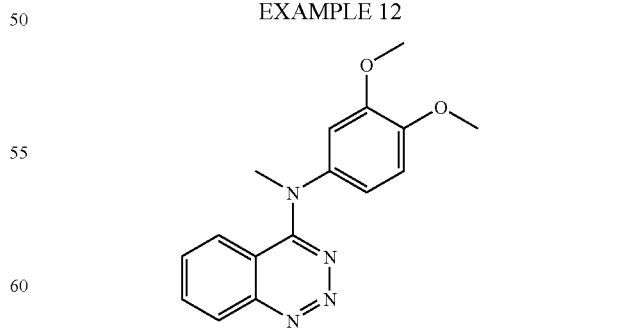

Benzo[d][1,2,3]triazin-4-yl-(3,4-dimethoxyphenyl)-methylamine

Benzo[d][1,2,3]triazin-4-yl-(3,4-dimethyoxyphenyl)-methylamine was synthesized using a procedure similar to (4-methoxyphenyl)-methyl-(6-methylbenzo[d][1,2,3]triazin-4-yl)-amine. The title compound was isolated in 3.4% yield. ¹H NMR (DMSO-d₆) δ 8.13 (ddd, 1 H), 7.89 (ddd, 1 H), 7.52 (ddd, 1 H), 7.12 (d, 1 H), 7.00 (d, 1 H), 6.83-6.90 (m, 2 H), 3.80 (s, 3 H), 3.70 (s, 3 H), 3.65 (s, 3 H). MS (ES) 297 (M+H).

EXAMPLE 13

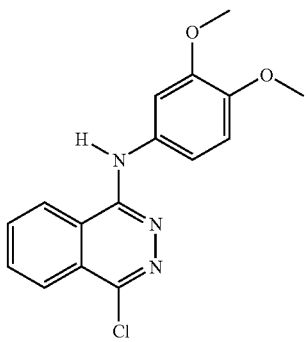

(4-chlorophthalazin-1-yl)-(3,4-dimethoxyphenyl)-amine (4-Chlorophthalazin-1-yl)-(3,4-dimethoxyphenyl)-amine was synthesized using a procedure similar to (4-chlorophthalazin-1-yl)-(3,4-dimethoxyphenyl)-methyl-amine. The crude product was purified via gradient MPLC (0-100%, EtOAc/hexanes, 30 min) to yield 45.5 mg (32%) of the title compound as a yellow solid. ¹H NMR (DMSO-d₆) δ 9.23 (br s, 1 H), 8.65 (d, 1 H), 8.20-8.02 (m, 2 H), 7.50 (d, 1 H), 7.45 (dd, 1 H), 6.98 (d, 1 H), 3.78 (s, 3 H), 3.77 (s, 3 H). MS (ES) 316 (M+H).

EXAMPLE 14

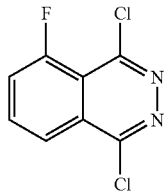

1,4-dichloro-5-fluorophthalazine 1,4-Dichloro-5-fluorophthalazine was synthesized using a procedure similar to 1,4-dichlorophthalazine. The title compound was isolated in 36% yield. ¹H NMR (DMSO-d₆) δ 8.21-8.31 (m, 2 H), 8.11 (ddd, 1 H). HRMS (ES) calcd for C₈H₃Cl₂N₂ (M+H) 216.9730, found 216.9725.

EXAMPLE 15

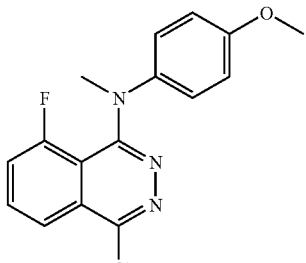

(4-Chloro-8-fluoro-phthalazin-1-yl)-
(4-methoxyphenyl)-methyl-amine

EXAMPLE 16

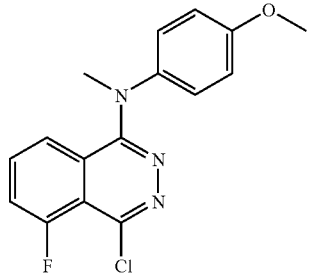

(4-Chloro-5-fluoro-phthalazin-1-yl)-
(4-methoxyphenyl)-methyl-amine

EXAMPLE 15 EXAMPLE 16

A solution of 1,4-dichloro-5-fluorophthalazine (79.5 mg, 0.44 mmol) and N-methyl-p-anisidine (78.0 mg, 0.57 mmol) in i-PrOH (3 mL) was heated to reflux for 1.5 h. The reaction mixture was cooled to rt and then concentrated onto a mixture of SiO₂ and Na₂CO₃. The reaction mixture was purified by two gradient MPLC columns (SiO₂, 0 to 100%, EtOAc/hexanes, 30 min; then SiO₂, 0 to 30%, EtOAc/hexanes, 30 min.) to provide 14.5 mg (15%) of the title compounds as a 2:1 mixture. Major Isomer: ¹H NMR (DMSO-d₆) δ 7.98-8.04 (m, 1 H), 7.77 (td, 1 H), 7.24 (ddd, 1 H), 6.85-6.91 (m, 2 H), 6.73-6.79 (m, 2H), 3.76 (s, 3 H), 3.59 (s, 3 H). MS (ES) 318 (M+H). Minor Isomer: ¹H NMR (DMSO-d₆) δ 7.44 (td, 0.5 H), 7.32-7.44 (m, 1 H), 6.97-7.04 (m, 1 H), 6.80-6.87 (m, 1 H), 3.79 (s, 1.5 H), 3.58 (s, 1.5 H). MS (ES) 318 (M+H).

EXAMPLE 17

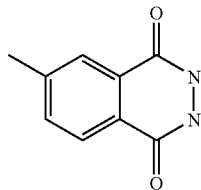

6-Methyl-2,3-dihydro-phthalazine-1,4-dione

A mixture of phthalic anhydride (2 g, 12.3 mmol), hydrazine hydrate (0.67 ml, 13.56 mmol) and AcOH (10 ml) was refluxed for 3 h. Upon heating the suspension went clear initially and then solid precipitated from solution. After 3 h the mixture was cooled to ambient temperature and the solid collected via vacuum filtration to provide 1.3 g (60%) of the title compound as a white solid. ¹H NMR (DMSO-d₆) δ 11.46 (s, 2 H), 7.97 (d, 1 H), 7.87 (s, 1 H), 7.7 (dd, 1 H), 2.51 (s, 3 H). MS (ES) 177 (M+H).

(m, 1 H), 7.00-7.05 (m, 4 H), 6.80-6.87 (m, 4 H), 3.80 (s, 3 H), 3.79 (s, 3 H), 3.58 (s, 6 H), 2.51 (s, 3 H), 2.28 (s, 3 H). MS (ES) 314 (M+H).

EXAMPLE 18

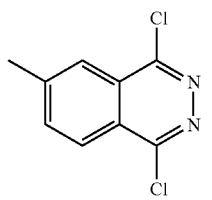

1,4-Dichloro-6-methyl-phthalazine

A mixture of 6-methyl-2,3-dihydro-phthalazine-1,4-dione (1.2 g, 6.86 mmol) and DMF (7 drops) in POCl₃ (10 ml) was refluxed for 2 h. The solution was cooled to ambient temperature and quenched by careful, dropwise addition into ice. The precipitate was collected via vacuum filtration providing 0.99 g (67%) of the title compound as a white solid. $^1$H NMR (DMSO-d$_6$) δ 8.27 (d, 1 H), 8.15-8.19 (m, 1 H), 8.10-8.14 (m, 1 H), 2.68 (s, 3 H). MS (ES) 213 (M+H).

EXAMPLE 19

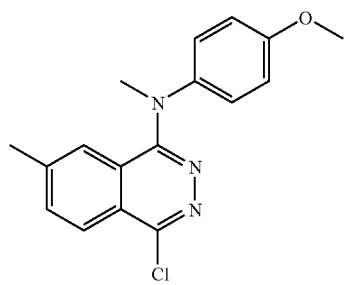

(4-Chloro-7-methyl-phthalazin-1-yl)-
(4-methoxyphenyl)-methyl-amine

EXAMPLE 20

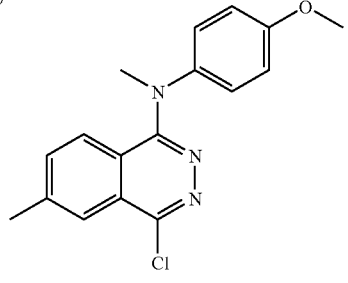

(4-Chloro-6-methyl-phthalazin-1
(4-methoxyphenyl)-methyl-amin

A mixture of 1,4-dichloro-6-methyl-phthalazine (0.8 g, 3.75 mmol) and (4-methoxyphenyl)-methyl-amine (0.61 g, 4.5 mmol) in isopropanol (10 mL) was refluxed for 2 h. The resulting mixture was diluted with EtOAc (10 ml), treated with Na₂CO₃ and evaporated onto SiO₂. The reaction mixture was purified by gradient MPLC (SiO₂, 0-100%, EtOAc/hexane, 40 min) to yield 0.74 g (64%) of the title compounds as a 1:1 mixture. $^1$H NMR (DMSO-d$_6$) δ 8.0 (d, 1 H), 7.91-7.94 (m, 1 H), 7.52-7.57 (m, 1 H), 7.30-7.33 (m, 2 H), 7.21-7.24

EXAMPLE 21

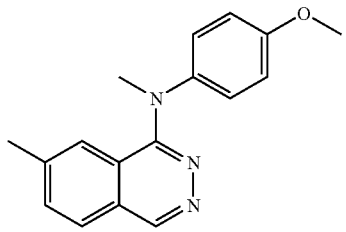

(4-Methoxyphenyl)-methyl-
(7-methyl-phthalazin-1-yl)-amine

EXAMPLE 22

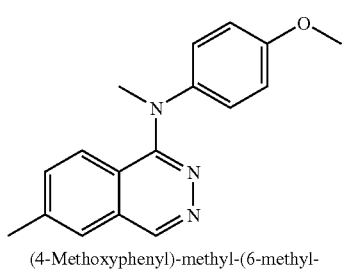

(4-Methoxyphenyl)-methyl-(6-methyl-
phthalazin-1-yl)-amine

A solution of a mixture of (4-chloro-7-methyl-phthalazine-1-yl)-(4-methoxyphenyl)-methyl-amine and (4-chloro-6-methyl-phthalazine-1-yl)-methyl-amine (0.1 g, 0.3 mmol) in MeOH (5 ml) was hydrogenated over 10% Pd/C overnight. The catalyst was filtered off, washing with MeOH. The filtrate was evaporated onto silica gel and purified by MPLC (SiO₂, 0-100%, EtOAc/hexane, 40 min) yielding 82 mg (92%) of the title compounds as a 1:1 mixture. $^1$H NMR (DMSO-d$_6$) δ 9.21 (d, 1 H), 9.17 (d, 1 H), 7.93 (d, 1H), 7.76-7.80 (m, 1 H), 7.64 (ddd, 1 H), 7.44 (ddd, 1 H), 7.21 (d, 1 H), 7.11-7.14 (m, 1H), 6.98-7.05 (m, 4 H), 6.86-6.93 (m, 4 H), 3.73 (s, 3 H), 3.72 (s, 3 H), 3.47 (s, 6 H), 2.44 (s, 3 H), 2.23 (s, 3 H). HRMS (ES) calcd for C₁₇H₁₈N₃O (M+H) 280.1444, found 280.1444.

EXAMPLE 23

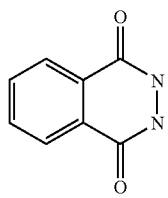

2,3-Dihydro-phthalazine-1,4-dione

A mixture of phthalic anhydride (1.0 g, 6.7 mmol), hydrazine hydrate (0.36 mL, 7.4 mmol, 1.1 eq) and acetic acid (10 mL) was refluxed for 3 h. Upon heating the suspension went clear initially and then a solid precipitated from solution. After 3 h the mixture was cooled to rt and the solid collected via vacuum filtration to provide 0.96 g (88%) of the title compound as a white solid was obtained. ¹H NMR (DMSO-d₆) δ 11.5 (br s, 2H), 8.08 (br s, 2 H), 7.80-7.95 (m, 2 H). MS (ES) 263 (M+H).

EXAMPLE 24

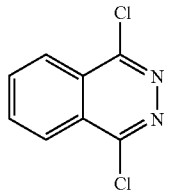

1,4-Dichloro-phthalazine

A mixture of 2,3-dihydro-phthalazine-1,4-dione (185 mg, 1.1 mmol) and DMF (5 drops) in POCl₃ (5 mL) was refluxed for 2 h. The solution was then cooled to rt and quenched by careful dropwise addition into ice. The product was then collected via vacuum filtration to provide 88.5 mg (39%) of the title compound as a white solid. ¹H NMR (DMSO-d₆) δ 8.34-8.42 (m, 2 H), 8.25-8.32 (m, 2 H). HRMS (ES) calcd for C₈H₅Cl₂N₂ (M+H) 198.9824, found 198.9832.

EXAMPLE 25

5-Fluoro-2,3-dihydrophthalazine-1,4-dione was synthesized using a procedure similar to 2,3-Dihydro-phthalazine-1,4-dione. The title compound was isolated in 86% yield. ¹H NMR (DMSO-d₆) δ 11.62 (br s, 2 H), 7.85-7.95 (m, 2 H), 7.63-7.72 (m, 1 H). MS (ES) 181 (M+H).

EXAMPLE 26

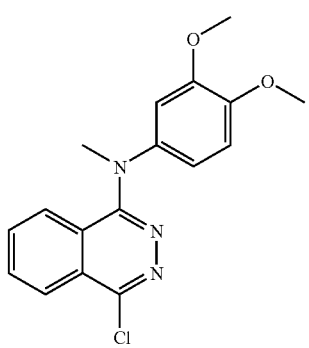

(4-Chlorophthalazin-1-yl)-(3,4-dimethoxyphenyl)-methyl-amine

A solution of 1,4-dichlorophthalazine (230 mg, 1.16 mmol) and (3,4-dimethoxyphenyl)-methyl-amine (134.0 mg, 0.80 mmol) was refluxed for 2 h in i-PrOH (3 mL). Upon cooling the solid was collected via vacuum filtration. The solid was dissolved in MeOH and then concentrated onto SiO₂ and Na₂CO₃. Purification by gradient MPLC (SiO₂, 0-50%, 30 min, EtOAc/hexanes) provided 119.6 mg (45%) of the title compound. ¹H

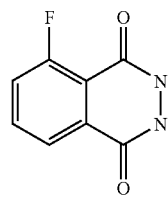

5-fluoro-2,3-dihydro-phthalazine-1,4-dione

NMR (DMSO-d₆) δ 8.15 (d, 1 H), 7.91 (ddd, 1 H), 7.73 (ddd, 1 H), 7.46 (d, 1 H), 6.97 (d, 1H), 6.82 (d, 1 H), 6.52 (dd, 1 H), 3.72 (s, 3 H), 3.70 (s, 3 H), 3.50 (s, 3 H). HRMS (ES) calcd for C₁₇H₁₇ClN₃O₂ 330.1004 (M+H). found 330.1009.

EXAMPLE 27

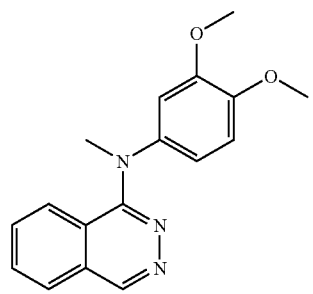

(3,4-Dimethoxyphenyl)-methylphthalazin-1-yl-amine (3,3-Dimethoxyphenyl)-methylphtalazin-1-yl-amine was synthesized using a procedure similar to (4-methoxyphenyl)-methyl-(7-methyl-phthalazin-1-yl)-amine. The title compound was isolated in 37% yield. ¹H NMR (CDCl₃) δ 9.13 (s, 1 H), 7.80 (d, 1 H), 7.67 (ddd, 1 H), 7.39-7.45 (m, 2 H), 6.78 (d, 1 H), 6.71 (d, 1 H), 6.64 (dd, 1 H), 3.88 (s, 3 H), 3.77 (s, 3 H), 3.65 (s, 3 H). ¹³C NMR (CDCl₃) δ 157.4, 150.1, 147.7, 146.9, 144.0, 131.1, 131.0, 128.8, 126.8, 125.9, 121.6, 117.3, 111.9, 109.1, 56.2, 56.2, 43.6. MS (ES) 296 (M+H).

EXAMPLE 28

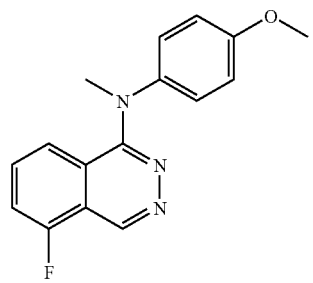

(5-Fluorophthalazin-1-yl)-(4-methoxyphenyl)-methyl-amine

5-Fluorophthalazin-1-yl)-(4-methoxyphenyl)-methyl-amine was synthesized using a procedure similar to (4-methoxyphenyl)-methyl-(7-methyl-phthalazin-1-yl)-amine. ¹H NMR (CDCl₃) 9.13 (d, 1 H), 7.69 (td, 1 H), 7.63 (dd, 1 H), 7.18 (ddd, 1 H), 6.86-6.92 (m, 2 H), 6.80-6.72 (m, 2 H), 3.76 (s, 3 H), 3.62 (s, 3 H). MS (ES) 284 (M+H).

EXAMPLE 29

Identification of Benzo[d][1,2,3]triazin-4-yl-(4-methoxy-phenyl)-methyl-amine and Analogs as Caspase Cascade Activators and Inducers of Apoptosis in Solid Tumor Cells Human breast cancer cell lines T-47D and DLD-1 were grown according to media component mixtures designated by American Type Culture Collection+10% FCS (Invitrogen Corporation), in a 5% $CO_2$-95% humidity incubator at 37° C. T-47D and DLD-1 cells were maintained at a cell density between 50 and 80% confluency at a cell density of 0.1 to $0.6 \times 10^6$ cells/mL. Cells were harvested at 600×g and resuspended at $0.65 \times 10^6$ cells/mL into appropriate media+10% FCS. An aliquot of 22.5 µL of cells was added to a well of a 384-well microtiter plate containing 2.5 µL of a 10% DMSO in RPMI-1640 media solution containing 0.16 to 100 µM of benzo[d][1,2,3]triazin-4-yl-(4-methoxyphenyl)-methyl-amine or other test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 µL of a solution containing 14 µM of N—(Ac-DEVD)-N'-ethoxycarbonyl-R110 fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for benzo[d][1,2,3]triazin-4-yl-(4-methoxy-phenyl)-methyl-amine or other test compounds to that of control samples. The $EC_{50}$ (nM) was determined by a sigmoidal dose-response calculation (Prism 3.0, GraphPad Software Inc.).

The caspase activity (Ratio) and potency ($EC_{50}$) are summarized in Table I:

TABLE I

Caspase Activity and Potency

| | T-47D (24 hr) | |
|---|---|---|
| Exa. Cmpd. | Ratio | $EC_{50}$ (nM) |
| 1 | 9.3 | 16 |
| 2 | 11.1 | 106 |

Thus, benzo[d][1,2,3]triazin-4-yl-(4-methoxy-phenyl)-methyl-amine and analogs are identified as potent caspase cascade activators and inducers of apoptosis and are thus useful in treating the various diseases and disorders discussed above.

EXAMPLE 30

Identification of Benzo[d][1,2,3]triazin-4-yl-(4-methoxy-phenyl)-methyl-amine and Analogs as Antineoplastic Compounds that Inhibit Cell Proliferation ($GI_{50}$)

T-47D, HT29, H1299, MX-1 and MDAMB435 cells were grown and harvested as in Example 29. An aliquot of 90 µL of cells ($4.4 \times 10^4$ cells/mL) was added to a well of a 96-well microtiter plate containing 5 µL of a 10% DMSO in RPMI-1640 media solution containing 10 nM to 100 µM of benzo[d][1,2,3]triazin-4-yl-(4-methoxy-phenyl)methyl-amine (1 nM to 10 µM final). An aliquot of 45 µL of cells was added to a well of a 96-well microtiter plate containing 5 µL of a 10% DMSO in RPMI-1640 media solution without compound as the control sample for maximal cell proliferation ($L_{Max}$). The samples were mixed by agitation and then incubated at 37° C. for 48 h in a 5% $CO_2$-95% humidity incubator. After incubation, the samples were removed from the incubator and 25 µL of CellTiter-Glo™ reagent (Promega) was added. The samples were mixed by agitation and incubated at room temperature for 10-15 min. Plates were then read using a luminescent plate reader (Model SPECTRAfluor Plus, Tecan) to give $L_{test}$ values.

Baseline for $GI_{50}$ (dose for 50% inhibition of cell proliferation) of initial cell numbers was determined by adding an aliquot of 45 µL of cells or 45 µL of media, respectively, to wells of a 96-well microtiter plate containing 5 µL of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 25 µL of CellTiter-Glo™ reagent (Promega) was added. The samples were mixed by agitation and incubated at 37° C. for 10-15 min at room temperature in a 5% $CO_2$-95% humidity incubator. Fluorescence was read as above, ($L_{start}$) defining luminescence for initial cell number used as baseline in $GI_{50}$ determinations.

Calculation:

$GI_{50}$ (dose for 50% inhibition of cell proliferation) is the concentration where $[(L_{Test} - L_{start})/(L_{Max} - L_{start})] = 0.5$.

The $GI_{50}$ (nM) are summarized in Table II:

TABLE II

| $GI_{50}$ in Cancer Cells | | |
|---|---|---|
| | $GI_{50}$ (nM) | |
| Cell Lines | Example 1 | Example 2 |
| T-47D | 50 | 120 |
| HT29 | 50 | 200 |
| H1299 | 40 | 106 |
| MX-1 | 50 | 52 |
| MDAMB435 | 7 | 62 |

Thus, benzo[d][1,2,3]triazin-4-yl-(4-methoxy-phenyl)-methyl-amine and analogs are identified as potent antineoplastic compounds that inhibit cell proliferation and are thus useful in treating the various diseases and disorders discussed above.

EXAMPLE 31

Inhibition of Tubulin Polymerization Assay

Lyophilized tubulin (Cytoskeleton #ML113, 1 mg, MAP-rich) is assayed for the effect of the test compound on tubulin polymerization as measured by change in fluorescence for 4',6-diamidino-2-phenylindole (DAPI) (Barron, D. M. et al. *Analytical Biochem.*, 2003, 315, 49-56.). One µl of serial dilutions of each test compound (from 100×DMSO stock) is added to a 96 well plate and preincubated for 30 minutes with 94 ul of the non-GTP supplemented tubulin supernatant. Five µl of DAPI/GTP solution is added to initiate polymerization and incubated for 30 minutes at 37° C. Fluorescence is read with excitation at 350 nm, emission at wavelength 485 nm on a Tecan Spectrafluor Plus. Polymerized tubulin (DMSO and with the tubulin stabilizer Taxol® (paclitaxel)) gives a higher DAPI fluorescence as compared to non-polymerized tubulin (vinblastine and colchicine used to determine baseline). The $IC_{50}$ for tubulin inhibition is the concentration found to decrease the fluorescence of DAPI by 50% as calculated with Prism 3.0.

EXAMPLE 32

Multidrug Resistant Cell Assays

Cytotoxicity of compounds in multidrug resistant cells can be determined by administering compounds to cell lines that overexpress the multidrug resistance pump MDR-1 and determining the viability of the cell lines. NCI-ADR/Res and P388/ADR cell lines are known to overexpress the multidrug resistance pump MDR-1 (also known as P-glycoprotein-1; Pgp-1); whereas MCF-7 and P388 cell lines do not overexpress the multidrug resistance pumps MDR-1, MRP-1, or BCRP.

NCI-ADR/Res, MCF-7, P388, and P388/ADR cell lines are obtained from American Type Culture Collection (Manassas, Va.) and maintained in RPMI-1640 media supplemented with 10% FCS, 10 units/ml penicillin and streptomycin, 2 mM Glutamax and 1 mM sodium pyruvate (Invitrogen Corporation, Carlsbad, Calif.). For compound testing, cells are plated in 96 well dishes at a concentration of $1.5 \times 10^4$ cells/well. Cells are allowed to adhere to the plate overnight and then incubated with compounds at final concentrations ranging from 0.13 nM to 10 uM for 72 hours. Cell viability is then assessed using the ATP-lite reagent (Perkin Elmer, Foster City, Calif.). Plates are read on a Wallac Topcount luminescence reader (Perkin Elmer, Foster City, Calif.) and the results graphed in Prism software (Graphpad Software, Inc., San Diego, Calif.). Non-linear regression with variable slope analysis is performed to obtain $IC_{50}$ concentration values.

EXAMPLE 33

Propidium Iodide and Annexin V Flow Cytometer-Based Assay to Detect Apoptosis

Necrotic versus apoptotic killing of human cell lines by compounds can be determined using dual annexin V-FITC and propidium iodide (PI) staining. Flipping of phosphatidylserine to the outer leaflet of the plasma membrane is a characteristic of all apoptotic cells. AnnexinV is a serum protein that binds to phosphatidylserine in the presence of the divalent cations (calcium). PI is a DNA stain that is excluded from live cells and is used to discriminate between cells with intact or damaged plasma membranes.

Cells are plated at varying densities in 6 well plates and treated with varying concentrations of compounds for 18-72 hours. Cells are grown in RPMI-1640 media supplemented with 10% FCS. DMSO concentrations do not exceed 0.1% v:v in any assay. All cells in the wells are harvested and rinsed 1× with cold Hanks buffered saline solution (HBSS) containing calcium and magnesium (Invitrogen, Carlsbad Calif.). Carefully aspirate supernatant after the wash and resuspend in 100 µl Annexin V-FITC (Annexin V/PT Apoptosis Detection Kit; R & D Systems TA4638; Minneapolis, Minn.) in binding buffer (10 mM HEPES pH 7.4, 150 mM NaCl, 5 mM KCl, 1 mM $MgCl_2$, 1.8 mM $CaCl_2$ and 2% bovine serum albumin w:v). Incubate in dark for 15 minutes on ice. Prior to analyzing samples, the volume is adjusted to 500 µl with 1× Binding Buffer and 25 µl PI is added per sample. Staining can be quantified on a flow cytometer (Becton-Dickenson, Franklin Lake, N.J.).

EXAMPLE 34

| Injection Formulation | |
|---|---|
| Excipients | Amount |
| Active Compound | 5 mg |
| PEG-400 | 5 grams |
| TPGS | 10 grams |
| Benzyl alcohol | 0.5 gram |
| Ethanol | 2 grams |
| D5W | Add to make 50 mL |

An injection formulation of a compound selected from Formulae I-VIII (the "Active Compound") can be prepared according to the following method. Five mg of the Active Compound is dissolved into a mixture of the d-α-tocopheryl polyethylene glycol 1000 succinate (TPGS), PEG-400, ethanol, and benzyl alcohol. D5W is added to make a total volume of 50 mL and the solution is mixed. The resulting solution is filtered through a 0.2 µm disposable filter unit and is stored at 25° C. Solutions of varying strengths and volumes are prepared by altering the ratio of Active Compound in the mixture or changing the total amount of the solution.

EXAMPLE 35

| Tablet Formulation | |
|---|---|
| Active Compound | 100.0 mg |
| Lactose | 100.0 mg |
| Corn Starch | 50.0 mg |
| Hydrogenated Vegetable Oil | 10.0 mg |
| Polyvinylpyrrolidone | 10.0 mg |
| | 270.0 mg |

A formulation of tablets of a compound selected from Formulae I-VIII (the "Active Compound") can be prepared according to the following method. One hundred mg of Active Compound) is mixed with 100 mg lactose. A suitable amount of water for drying is added and the mixture is dried.

The mixture is then blended with 50 mg of corn starch, 10 mg hydrogenated vegetable oil, and 10 mg polyvinylpyrrolidinone. The resulting granules are compressed into tablets. Tablets of varying strengths are prepared by altering the ratio of Active Compound in the mixture or changing the total weight of the tablet.

EXAMPLE 36

| Capsule Formulation | |
|---|---|
| Active Compound | 100.0 mg |
| Microcrystalline Cellulose | 200.0 mg |
| Corn Starch | 100.0 mg |
| Magnesium Stearate | 400.0 mg |
| | 800.0 mg |

A formulation of capsules containing 100.0 mg of a compound selected from Formulae I-VIII (the "Active Compound") can be prepared according to the following method. One hundred mg of Active Compound is mixed with 200 mg of microcrystalline cellulose and 100 mg of corn starch. Four hundred mg of magnesium stearate is then blended into the mixture and the resulting blend is encapsulated into a gelatin capsule. Doses of varying strengths can be prepared by altering the ratio of the Active Compound to pharmaceutically acceptable carriers or changing the size of the capsule.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A pharmaceutical composition comprising an effective amount of a compound having a structure according to Formula II:

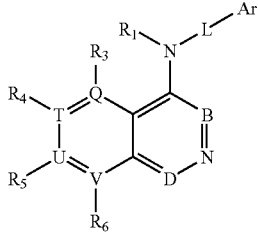

(II)

or a pharmaceutically acceptable salt thereof, wherein:
Ar is aryl or heteroaryl; each of which is optionally substituted by one or more substituents;
L is —($CR_aR_b$)n- or —$N(R_a)C(=O)$— wherein n is 0, 1 or 2, and $R_a$ and $R_b$ independently are H, optionally substituted alkyl, methyl, ethyl, propyl, isopropyl, or $C_{1-4}$ haloalkyl;
$R_1$ is $C_{1-6}$ alkyl;
B is nitrogen;
D is nitrogen;
$R_3$-$R_6$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$, (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{52})(R^{53})$, —$N(R^{52})C(=O)R_{42}$, —$N(R^{52})C(=O)N(R^{52})(R^{53})$, —$C(=O)N(R^{52})(R^{53})$, —$OC(=O)N(R^{52})(R^{53})$, $R_{42}C(=O)$—, $R_{42}C(=O)O$—, $R_{42}C(=G^1)$-, $R_{42}C(=G^1)G^2$-, $R_{42}C(=G^1)G^2(R^{52})$—, —$C(=G^1)G^2R_{43}$, or —$G^4C(=G^1)G^2R_{43}$, (d) —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C(=G^1)G^2R_{41}$ or -$G^3C(=G^1)G^2R_{41}$, $G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl;

$R^{52}$ and $R^{53}$ are independently H, OH ($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and Q, T, U, and V are carbon; and another anticancer agent selected from the group consisting of alkylating agents, antimitotic agents, topo I inhibitors, topo II inhibitors, RNA/DNA antimetabolites, EGFR inhibitors, angiogenesis inhibitors, tubulin inhibitors, proteosome inhibitors, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® and alanosine.

2. The pharmaceutical composition of claim 1 wherein $R_1$ is $C_{1-2}$ alkyl.

3. The pharmaceutical composition of claim 2, wherein $R_3$-$R_6$, are independently $R_{14}$, $OR_{14}$, $SR_{14}$ or $NR_{14}R_{15}$, wherein $R_{14}$ and $R_{15}$ are independently H, halo, hydroxyl, carboxyl, $C_{1-6}$ alkyl, $C_2$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy.

4. The pharmaceutical composition of claim 3 wherein $R_5$ is H, F, or $C_{1-3}$ alkyl.

5. A compound having a structure according to Formula III:

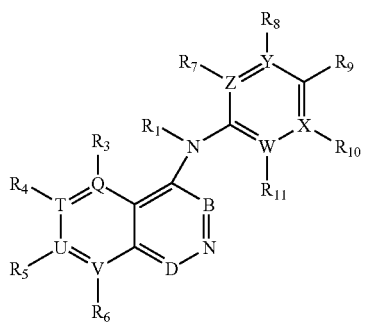

(III)

or a pharmaceutically acceptable salt thereof, wherein:
$R_1$ is $C_{1-6}$ alkyl;
B is nitrogen;
D is nitrogen;
$R_3$-$R_{11}$ are independently selected from:
(a) H, halo, $N_3$, nitro, hydroxy, thiol, and CN,
(b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{52}$)($R^{53}$), —N($R^{52}$)C(=O)$R_{42}$, —N($R^{52}$)C(=O)N($R^{52}$)($R^{53}$), —C(=O)N($R^{52}$)($R^{53}$), —OC(=O)N($R^{52}$)($R^{53}$), $R_{42}$C(=O)—, $R_{42}$C(=O)O—, $R_{42}$C(=$G^1$)-, $R_{42}$C(=$G^1$)$G^2$-, $R_{42}$C(=$G^1$)$G^2$($R^{52}$)—, —C($G^1$)$G^2R_{43}$, -$G^4$C(=$G^1$)$G^2R_{43}$, (d) —N($R^{50}$)($R^{51}$), —N($R^{50}$)C(=O)$R_{40}$, —N($R^{50}$)C(=O)N($R^{50}$)($R^{51}$), —C(=O)N($R^{50}$)($R^{51}$), —OC(=O)N($R^{50}$)($R^{51}$), $R_{40}$C(=O)—, $R_{40}$C(=O)O—, $R_{40}$C(=$G^1$)-, $R_{40}$C(=$G^1$)$G^2$-, $R_{40}$C(=$G^1$)$G^2$($R^{50}$)—, —C(=$G^1$)$G^2R_{41}$ or -$G^3$C(=$G^1$)$G^2R_{41}$, $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$ and $R^{53}$ are independently H, OH ($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and Q, T, U, and V are carbon, W, X, Y, and Z are independently nitrogen or carbon, two of W, X, Y, and Z are nitrogen, provided that when W, X, Y, or Z are nitrogen then there is no substituent at the nitrogen.

6. A compound having a structure according to Formula IV:

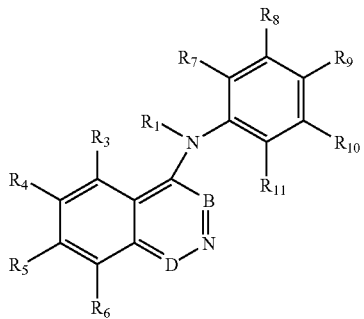

(IV)

or a pharmaceutically acceptable salt thereof, wherein $R_1$ is $C_{1-6}$ alkyl;

B is nitrogen;

D is nitrogen;

$R_3$-$R_{11}$ are independently selected from:

(a) H, halo, $N_3$, nitro, hydroxy, thiol, and CN, (b) $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{1-10}$ hydroxyalkyl, $C_{1-6}$ alkyl-O—$C_{1-6}$ alkyl-, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$—, $R_{40}C(=O)O$—, $R_{40}C(=G^1)$-, $R_{40}C(=G^1)G^2$-, $R_{40}C(=G^1)G^2(R^{50})$—, —$C)(=G^1)G^2R_{41}$ or -$G^3C(=G^1)G^2R_{41}$, (c) carbocycle, heterocycle, aryl, and heteroaryl, each of which being optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{52})(R^{53})$, —$N(R^{52})C(=O)R_{42}$, —$N(R^{52})C(=O)N(R^{52})(R^{53})$, —$C(=O)N(R^{52})(R^{53})$, —$OC(=O)N(R^{52})(R^{53})$, $R_{42}C(=O)$—, $R_{42}C(=O)O$—, $R_{42}C(=G^1)$-, $R_{42}C(=G^1)G^2$-, $R_{42}C(=G^1)G^2(R^{52})$-, —$C(=G^1)G^2R_{43}$, or -$G^4C(=G^1)G^2R_{43}$, (d) —$N(R^{50})(R^{51})$, —$N(R^{50})C(=O)R_{40}$, —$N(R^{50})C(=O)N(R^{50})(R^{51})$, —$C(=O)N(R^{50})(R^{51})$, —$OC(=O)N(R^{50})(R^{51})$, $R_{40}C(=O)$-, $R_{40}C(=O)O$—, $R_{40}C(=G^1)$-, $R_{40}C(=G^1)G^2$-, $R_{40}C(=G^1)G^2(R^{50})$-, —$C(=G^1)G^2R_{41}$ or -$G^3C(=G^1)G^2R_{41}$, $G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl, carbocycle, heterocycle, aryl and heteroaryl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$ and $R^{51}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, carbocycle, heterocycle, aryl, heteroaryl, or $R^{50}$ and $R^{51}$ together with the nitrogen atom to which they are both linked form a 3, 4, 5 or 6-membered heterocycle, wherein $R^{50}$ and $R^{51}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl; and $R^{52}$ and $R^{53}$ are independently H, OH ($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with one to three substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl;

with the proviso that $R_9$ is not halo, and if $R_9$ is H, then $R_8$ and $R_{10}$ are not H or halo.

7. The compound of claim 6, wherein $R_1$ is $C_{1-2}$ alkyl.

8. The compound of claim 7, wherein $R_3$, $R_4$, $R_6$-$R_8$, $R_{10}$, and $R_{11}$ are independently $R_{14}$, $OR_{14}$, $SR_{14}$ or $NR_{14}R_{15}$, wherein $R_{14}$ and $R_{15}$ are independently H, halo, hydroxyl, carboxyl, $C_{1-6}$ alkyl, $C_{2-6}$ alkenyl, $C_{2-6}$ alkynyl, or $C_{1-6}$ haloalkyl; wherein any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy.

9. The compound of claim 8, wherein $R_5$ is H, F, or $C_{1-3}$ alkyl.

10. The compound of claim 9, wherein $R_9$ is H; OH; halo; $N_3$; $C_{1-6}$ alkyl; $C_{1-6}$ haloalkyl —$OR_{9a}$, wherein $R_{9a}$ is $C_{1-6}$ alkyl or $C_{1-6}$ haloalkyl; —$NH(R^a)$ or —$N(R^a)(R^b)$ where $R^a$ and $R^b$ are independently $C_{1-6}$ alkyl, $C_{1-6}$ acyl, $C_{1-6}$ acyloxy, amino, —$(C=O)N(R^c)(R^d)$ wherein $R^c$ and $R^d$ are independently H or $C_{1-6}$ alkyl; or —$COOR_{9b}$, wherein $R_{9b}$ is $C_{1-6}$ alkyl; optionally $R_9$ and one of $R_8$ and $R_{10}$ together form a 3, 4, 5, or 6-membered heterocycle; and any of the groups are optionally substituted with one or more halo, $C_{1-6}$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_{1-6}$ acylamino, hydroxy, thiol, $C_{1-6}$ acyloxy, azido, $C_1$-$C_6$ alkoxy, carboxy or $C_{1-2}$ alkylenedioxy.

11. The compound of claim 9, wherein $R_9$ is chosen from:
   —$OR_{19}$, wherein $R_{19}$ is selected from the group of methyl, ethyl, fluoromethyl, and fluoroethyl;
   —$NHCH_3$;
   —$N(CH_3)_2$;
   —$N_3$;
   —$COOR_{20}$; and
   —$NC(O)N(R_{21})(R_{22})$ or —$NC(O)R_{20}$ wherein $R_{20}$ is methyl or ethyl; and $R_{21}$ and $R_{22}$ are independently H, methyl or ethyl.

12. A compound according to claim 6 wherein the compound is chosen from:
   Benzo[d][1,2,3]triazin-4-yl-(4-methoxy-phenyl)-methyl-amine;
   (4-Methoxyphenyl)-methyl-(6-methylbenzo [d][1,2,3]triazin-4-yl)-amine;
   (4-Methoxyphenyl)-methyl-(7-methylbenzo [d][1,2,3]triazin-4-yl)-amine;
   (5-Fluoro-benzo[d][1,2,3]triazin-4-yl)-(4-methoxyphenyl)-methyl-amine;
   Benzo[d][1,2,3]triazin-4-yl-(3,4-dimethyoxyphenyl)-methyl-amine; and
   pharmaceutically acceptable salts thereof.

13. A pharmaceutical composition comprising an effective amount of a compound according to claim 6, and a pharmaceutically acceptable carrier.

14. A pharmaceutical composition comprising an effective amount of a compound according to claim 5, and a pharmaceutically acceptable carrier.

* * * * *